(12) United States Patent
Stupple

(10) Patent No.: US 11,028,101 B2
(45) Date of Patent: Jun. 8, 2021

(54) 3-OXA-8-AZABICYCLO[3.2.1]OCTANE DERIVATIVES AND THEIR USE IN THE TREATMENT OF CANCER AND HEMOGLOBINOPATHIES

(71) Applicant: CTXT PTY LTD, Victoria (AU)

(72) Inventor: Paul Anthony Stupple, Victoria (AU)

(73) Assignee: CTXT PTY LTD, Victoria (AU)

( * ) Notice: Subject to any disclaimer, the term of this patent is extended or adjusted under 35 U.S.C. 154(b) by 0 days.

(21) Appl. No.: 16/687,401

(22) Filed: Nov. 18, 2019

(65) Prior Publication Data

US 2020/0087320 A1 Mar. 19, 2020

Related U.S. Application Data

(62) Division of application No. 16/082,256, filed as application No. PCT/EP2017/055536 on Mar. 9, 2017, now Pat. No. 10,519,167.

(30) Foreign Application Priority Data

Mar. 9, 2016 (GB) .................................. 1604029.7

(51) Int. Cl.
C07D 498/08 (2006.01)
C07D 217/16 (2006.01)
A61K 31/5386 (2006.01)
A61K 45/06 (2006.01)

(52) U.S. Cl.
CPC ........ *C07D 498/08* (2013.01); *A61K 31/5386* (2013.01); *A61K 45/06* (2013.01); *C07D 217/16* (2013.01)

(58) Field of Classification Search
CPC ................ C07D 498/08; C07D 217/16; A61K 31/5386; A61K 45/06
USPC ...................................................... 514/230.5
See application file for complete search history.

(56) References Cited

U.S. PATENT DOCUMENTS 4,880,802 A 11/1989 Schohe et al.
6,008,219 A 12/1999 Stemp et al.
(Continued)

FOREIGN PATENT DOCUMENTS

CN 102417483 A 4/2012
DE 261 153 A1 10/1988
(Continued)

OTHER PUBLICATIONS

Aggarwal et al., Cancer Cell 2010, 18, 329-340.
(Continued)

*Primary Examiner* — Niloofar Rahmani
(74) *Attorney, Agent, or Firm* — Stites & Harbison PLLC; Richard S. Myers, Jr.

(57) ABSTRACT

A compound of formula Ia, Ib, Ic or Id:

(Ia)

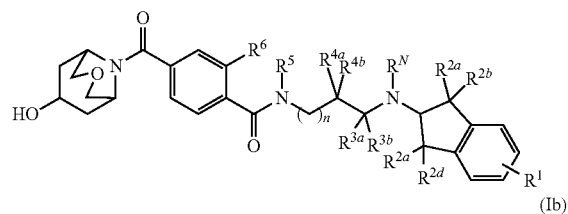

(Ib)

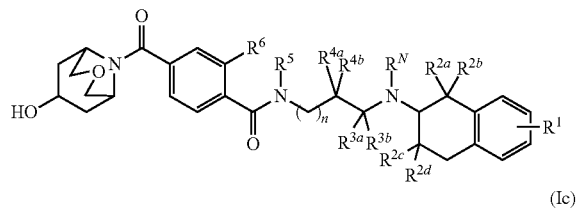

(Ic)

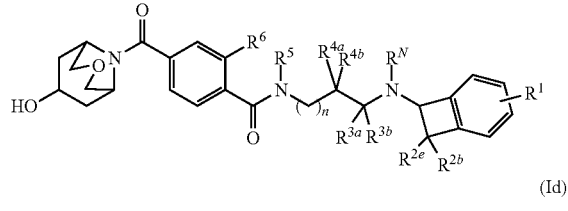

(Id)

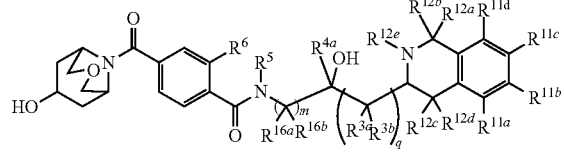

wherein: n is 1 or 2; $R^N$ is H or Me; $R^1$ is optionally one or more halo or methyl groups; $R^{2a}$ and $R^{2b}$ are independently selected from the group consisting of: (i) F; (ii) H; (iii) Me; and (iv) $CH_2OH$; $R^{2c}$ and $R^{2d}$ (if present) are independently selected from the group consisting of: (i) F; (ii) H; (iii) Me; and (iv) $CH_2OH$; $R^{3a}$ and $R^{3b}$ are independently selected from H and Me; $R^{4a}$ is selected from OH, $-NH_2$, $-C(=O)NH_2$, and $-CH_2OH$; $R^{4b}$ is either H or Me; $R^5$ is either H or Me; m is 1 or 2; q is 0 or 1; $R^{11a}$, $R^{11b}$, $R^{11c}$ and $R^{11d}$ are independently selected from H, halo, $C_{1-4}$ alkyl, $C_{1-4}$ fluoroalkyl, $C_{3-4}$ cycloalkyl, $C_{1-4}$ alkyloxy, $NH-C_{1-4}$ alkyl and cyano; $R^{12a}$ and $R^{12b}$ are independently selected from the group consisting of: (i) F; (ii) H; (iii) Me; and (iv) $CH_2OH$; $R^{12c}$ and $R^{12d}$ are independently selected from the group consisting of: (i) F; (ii) H; (iii) Me; and (iv) $CH_2OH$; $R^{12e}$ is H or Me; $R^{13a}$ and $R^{13b}$ are independently selected from H and Me; $R^{14}$ is either H or Me; $R^{16a}$ and $R^{16b}$ are independently selected from H and Me; $R^6$ is selected from H, OMe, and OEt.

2 Claims, No Drawings

(56) References Cited

U.S. PATENT DOCUMENTS

| | | | |
|---|---|---|---|
| 6,046,210 | A | 4/2000 | Stemp et al. |
| 6,274,593 | B1 | 8/2001 | Johns et al. |
| 6,579,892 | B1 | 6/2003 | Starck et al. |
| 8,648,079 | B2 | 1/2014 | Koike |
| 9,856,252 | B2 | 1/2018 | Stupple et al. |
| 10,005,792 | B2 | 6/2018 | Bergman et al. |
| 2005/0101647 | A1 | 5/2005 | Oda et al. |
| 2005/0107398 | A1 | 5/2005 | Mach et al. |
| 2006/0235037 | A1 | 10/2006 | Purandare et al. |
| 2010/0069431 | A1 | 3/2010 | Iwata et al. |
| 2016/0222005 | A1 | 8/2016 | Stupple et al. |
| 2017/0283407 | A1 | 10/2017 | Foitzik et al. |
| 2017/0298075 | A1 | 10/2017 | Berman et al. |

FOREIGN PATENT DOCUMENTS

| | | | |
|---|---|---|---|
| EP | 1008592 | A2 | 6/2000 |
| GB | 2286395 | A | 6/1995 |
| WO | WO 96/30333 | A1 | 10/1996 |
| WO | WO 97/43262 | A1 | 11/1997 |
| WO | WO 98/49145 | A1 | 11/1998 |
| WO | WO 03/035065 | A1 | 5/2003 |
| WO | WO 03/082186 | A2 | 10/2003 |
| WO | WO 2004/016611 | A1 | 2/2004 |
| WO | WO 2004/024897 | A2 | 3/2004 |
| WO | WO 2005/030206 | A1 | 4/2005 |
| WO | WO 2005/042495 | A1 | 5/2005 |
| WO | WO 2006/008133 | A2 | 1/2006 |
| WO | WO 2006/080821 | A1 | 8/2006 |
| WO | WO 2009/005551 | A2 | 1/2009 |
| WO | WO 2009/113085 | A1 | 9/2009 |
| WO | WO 2009/139076 | A1 | 11/2009 |
| WO | WO 2010/025295 | A2 | 3/2010 |
| WO | WO 2012/108689 | A2 | 8/2012 |
| WO | WO 2014/100695 | A1 | 6/2014 |
| WO | WO 2014/100716 | A1 | 6/2014 |
| WO | WO 2014/100719 | A2 | 6/2014 |
| WO | WO 2014/100730 | A1 | 6/2014 |
| WO | WO 2014/100734 | A1 | 6/2014 |
| WO | WO 2014/100764 | A2 | 6/2014 |
| WO | 2016034673 | * | 9/2015 |
| WO | WO 2015/198229 | A1 | 12/2015 |
| WO | WO 2015/200677 | A2 | 12/2015 |
| WO | WO 2016/034671 | A1 | 3/2016 |
| WO | WO 2016/034673 | A1 | 3/2016 |
| WO | WO 2016/034675 | A1 | 3/2016 |

OTHER PUBLICATIONS

Berger, Nat. Cell Biol. 2008, 10, 1389-1390.
Chen et al., Proc. Natl. Acad. Sci. USA 2009, 106, 13433-13438.
Cho et al., EMBO J. 2012, 31, 1785-1797.
Durant et al., Cell Cycle 2009, 8, 801-802.
Gu et al., Biochem. J. 2012, 446, 235-241.
He et al., J. Transl. Med. 2013, 11:14.
Jansson et al., Nat. Cell Biol 2008, 10, 1431-1439.
Kanduri et al., Blood 2010, 115, 296-305.
Kim et al., Clin. Cancer Res. 2005, 11, 473-482.
Krause et al., Pharmacol. Ther. 2007, 113, 50-87.
Le Guezennec et al., Mol. Cell Biol. 2006, 26, 843-851.
Nicholas et al., Cancer Res. 2012, 72(8), Supplement, DOI : 10.1158/1538-7445.AM2012-LB-254.
Pal et al., Mol Cell. Biol. 2003, 23, 7475-7487.
Pal et al., EMBO J. 2007, 26, 3558-3569.
Pollack et al., J. Biol. Chem. 1999, 274, 31531-31542.
Powers et al., Cancer Res. 2011, 71, 5579-5588.
Rank et al., Blood 2010, 116, 1582-1592.
Scoumanne et al., Nucleic Acids Res. 2009, 37, 4965-4976.
Wang et al., Mol. Cell Biol. 2008, 28, 6262-6277.
Zhongping et al., PLoS ONE 2012, 7(8): e44033.
Zhang et al., J. Pestic. Sci. 2012, 37, 338-341.
Secci et al., J. Heterocyclic Chem. 2012, 49, 1187-1195.
Rostamizadeh et al., Synth. Commun. 2011, 41, 1794-1804.
Chen et al., Heterocycl. Commun. 2010, 16, 123-135.
Göker et al., J. Heterocyclic Chem. 2009, 46, 936-948.
Kaynak et al., Stuct. Chem. 2008, 19, 477-480.
Kuş et al., Ankara Ecz. Fak. Derg. 2006, 35, 237-244.
Vijayakumar et al., J. Chem. Pharm Res. 2010, 2(4), 215-224.
Richards et al., Eur. J. Med. Chem. 2006, 41, 950-969.
Mach et al., ChemBioChem 2004, 5, 508-518.
Braun et al., Ber. Dtsch. Chem. Ges., B 1926, 59, 2416-2425.
Zajdel et al., QSAR Comb. Sci. 2007, 26, 215-219.
Chan-Penebre et al., Nature Chemical Biology, 2015, 11, 432-437.

* cited by examiner

3-OXA-8-AZABICYCLO[3.2.1]OCTANE DERIVATIVES AND THEIR USE IN THE TREATMENT OF CANCER AND HEMOGLOBINOPATHIES

CROSS REFERENCE TO RELATED APPLICATIONS

This is a divisional of U.S. application Ser. No. 16/082,256, now allowed, which is a § 371 National Stage Application of PCT/EP2017/055536 filed Mar. 9, 2017 which claims priority to GB 1604029.7, filed Mar. 9, 2016.

The present invention relates to amino-bicyclic compounds and their use as pharmaceuticals, and in particular, in treating cancer and hemoglobinopathies.

BACKGROUND TO THE INVENTION

Post-translational modification of proteins is a hallmark of signal transduction where cells are able to react quickly to changes or events in the cellular environment. Post-translational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important post-translational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two ψ-guanidino nitrogen atoms and the internal δ-guanidino nitrogen atom. Mono-methylation and dimethylation of arginine (MMA and DMA) is found in mammalian cells at one or both of the two ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom. Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with post-translational modifications. Phosphorylation was one of the first post-translational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these post-translational modifications. However, despite the plethora of post-translational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a pro-survival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoglobinopathies

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by subunits as the infant grows. The developmental switch in human ß-like globin gene subtype from foetal (γ) to adult (ß) that begins at birth heralds the onset of the hemoglobinopathies ß-thalassemia and sickle cell disease (SCD). In ß-thalassemia the adult chains are not produced. In SCD a point mutation in the coding sequence in the ß globin gene leads to the production of a protein with altered polymerisation properties. The observation that increased adult γ-globin gene expression (in the setting of hereditary persistence of foetal hemoglobin (HPFH) mutations) significantly ameliorates the clinical severity of ß-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia and Sickle Cell Disease (SCD).

The present inventors have developed particular substituted β-hydroxy amides inhibit the activity of PRMT5 and therefore may be of use in treating conditions ameliorated by the inhibition of the activity of PRMT5.

SUMMARY OF THE INVENTION

A first aspect of the present invention provides a compound of formula Ia, Ib, Ic or Id:

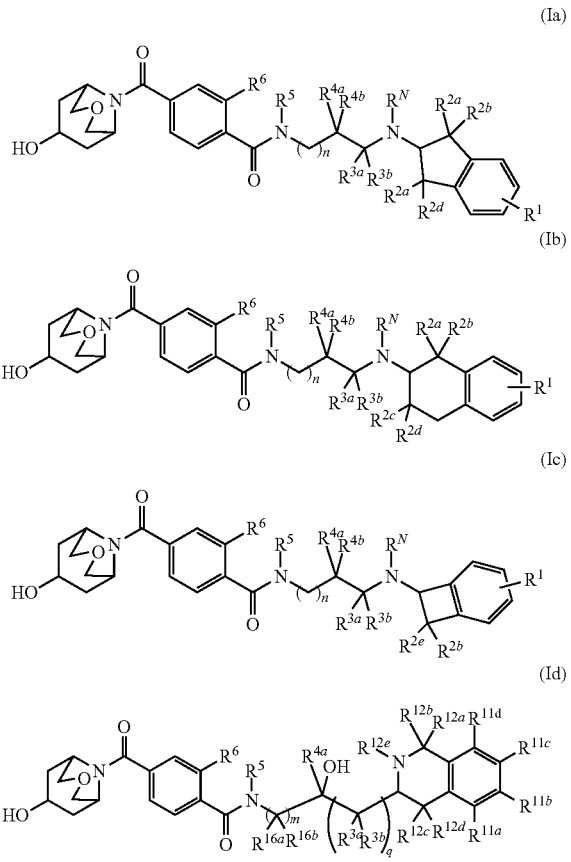

wherein:

n is 1 or 2;

$R^N$ is H or Me;

$R^1$ is optionally one or more halo or methyl groups;

$R^{2a}$ and $R^{2b}$ are independently selected from the group consisting of:
 (i) F;
 (ii) H;
 (iii) Me; and
 (iv) $CH_2OH$;

$R^{2c}$ and $R^{2d}$ (if present) are independently selected from the group consisting of:
 (i) F;
 (ii) H;
 (iii) Me; and
 (iv) $CH_2OH$;

$R^{3a}$ and $R^{3b}$ are independently selected from H and Me;

$R^{4a}$ is selected from OH, $-NH_2$, $-C(=O)NH_2$, and $-CH_2OH$;

$R^{4b}$ is either H or Me;

$R^5$ is either H or Me;

m is 1 or 2;

q is 0 or 1;

$R^{11a}$, $R^{11b}$, $R^{11c}$ and $R^{11d}$ are independently selected from H, halo, $C_{1-4}$ alkoxy, $C_{1-4}$ alkyl, $C_{1-4}$ fluoroalkyl, $C_{3-4}$ cycloalkyl, $NH-C_{1-4}$ alkyl or cyano;

$R^{12a}$ and $R^{12b}$ are independently selected from the group consisting of:
 (i) F;
 (ii) H;
 (iii) Me; and
 (iv) $CH_2OH$;

$R^{12c}$ and $R^{12d}$ are independently selected from the group consisting of:
 (i) F;
 (ii) H;
 (iii) Me; and
 (iv) $CH_2OH$;

$R^{12e}$ is H or Me;

$R^{13a}$ and $R^{13b}$ are independently selected from H and Me;

$R^{14}$ is either H or Me;

$R^{16a}$ and $R^{16b}$ are independently selected from H and Me;

$R^6$ is selected from H, OMe, and OEt; or a compound of formula:

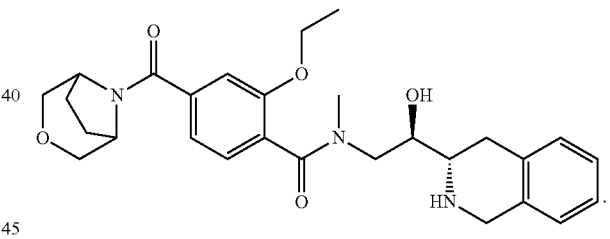

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment of cancer, comprising administering to a patient in need of treatment, a compound of the first aspect of the invention or a pharmaceutical composition of the first aspect of the invention. The third aspect of the present invention also provides the use of a compound of the first aspect of the invention in the manufacture of a medicament for treating cancer, and a compound of the first aspect of the invention or pharmaceutical composition thereof for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemoglobinopathies, comprising administering to a patient in need of treatment, a compound of the first aspect of the invention or a pharmaceutical composition of the first aspect of the invention. The fourth aspect of the present invention also provides the use of a compound of the first aspect of the invention in the manufacture of a medicament for treating hemoglobinopathies, and a compound of the first aspect of the invention or pharmaceutical composition of the first aspect of the invention for use in the treatment of hemoglobinopathies.

Definitions

Halo: The term "halo" as used herein, refers to a group selected from fluoro, chloro, bromo and iodo.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{1-4}$ fluoroalkyl: The term "$C_{1-4}$ fluoroalkyl" refers to a $C_{1-4}$ alkyl group as defined above where one of more of the hydrogen atoms is replaced by a fluoro. Examples of $C_{1-4}$ fluoroalkyl include, but are not limited to, —$CF_3$, $CF_2H$, —$C_2F_5$, and —$C_2F_4H$.

$C_{3-4}$ cycloalkyl: the term '$C_{3-4}$ cycloalkyl' as used herein, pertains to a monovalent moiety obtained by removing a hydrogen atom from a carbon atom of a saturated cyclic core having 3 or 4 atoms in the cyclic core all of which are carbon atoms. Examples of $C_{3-4}$ cycloalkyl include cyclopropyl and cyclobutyl.

$C_{1-4}$ alkoxy: the term "$C_{1-4}$ alkoxy" as used herein, pertains to a group —OP, where P is $C_{1-4}$ alkyl as defined above.

Cyano: the term 'cyano' as used herein, pertains to a moiety —CN.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO), a salt or solvate thereof, as well as conventional protected forms. Similarly, a reference to an amino group includes the protonated form (–N+$HR^1R^2$), a salt or solvate of the amino group, for example, a hydrochloride salt, as well as conventional protected forms of an amino group. Similarly, a reference to a hydroxyl group also includes the anionic form (—O), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchephonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

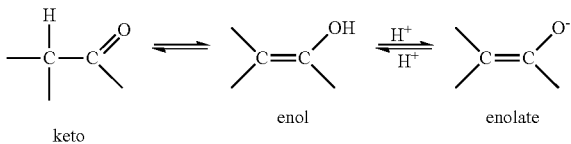

keto — enol — enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemoglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoglobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemoglobinopathy is a condition associated with the presence of abnormal hemoglobin in the blood of a subject. Such conditions include ß-thalassemia and Sickle Cell Disease, α-thalassemia and δ-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial cell growth factor receptor 3 (VEGFR3) antibody IMC-3C$_5$, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesis the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formulae Ia, Ib and Ic

Compounds of formulae Ia, Ib and Ic, as described above, can be prepared by synthetic strategies outlined below, wherein the definitions above apply. The synthetic strategies could be applied to the use of racemic or single enantiomer starting materials.

General Synthesis Method 1

Scheme 1A illustrates the formation of the amide bond by coupling a relevant carboxylic acid to a primary amine or a secondary amine G1. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester.

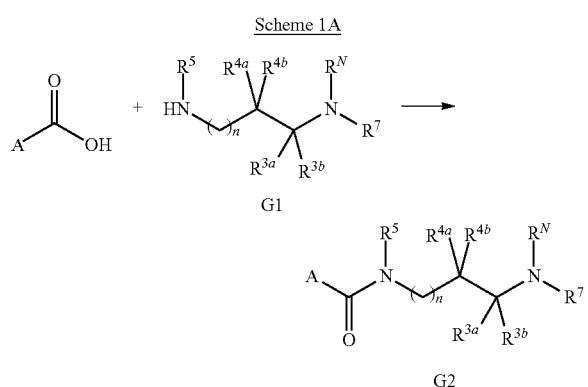

G1

G2

$R^7$ represents the fused cyclic system.

Optionally, where $R^N$=H, a protecting group (PG) may be used such as but not limited to Boc, allyl, benzyl, 2,4-dimethoxybenzyl. As illustrated in Scheme 1B, coupling between a relevant carboxylic acid or activated acid, e.g. acyl halide to a primary amine or a secondary amine G3 bearing a protecting group (PG) is performed as described previously. Conditions for the removal of the protecting group are dependent on the type of protecting group employed, and may include but is not limited to such methods as acid hydrolysis, transition metal catalysed cleavage and hydrogenation over transition metal catalysts. Other suitable protecting groups and removal methods will be known to those skilled in the art (for example *Greene's Protective Groups in Organic Synthesis, 4th Edition*). The use of such a protecting group could be relevant in the other Schemes described.

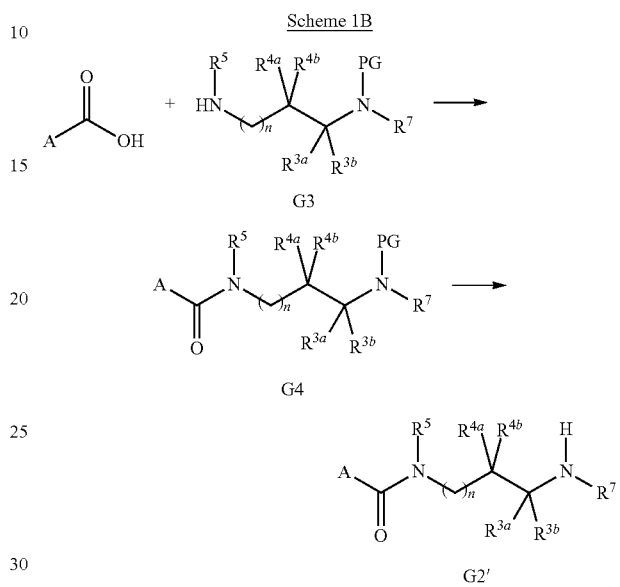

Where A contains a direct carboxylic acid substitution or a further substitution that also has a carboxylic acid substitution G5, another amide formation can be conducted to provide compounds of G6, scheme 1C.

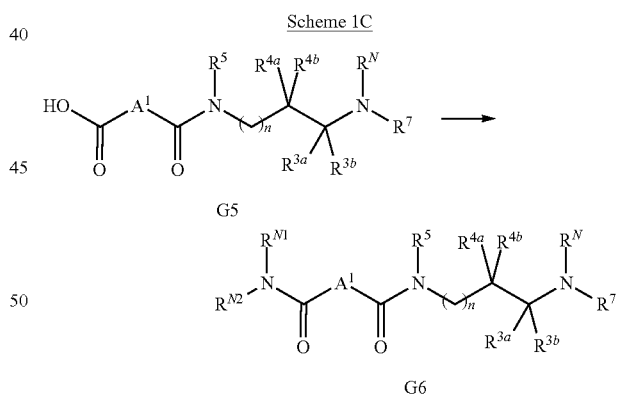

General Synthesis Method 2

Scheme 2A illustrates the synthesis of the substituted amine alcohol G9. This is achieved by opening the epoxide with a desired amine (HNR$^N$R$^7$) to form the intermediate G7. The phthalimide protecting group can then be removed by heating with hydrazine hydrate to form G8. Other suitable protecting groups and removal methods will be known to those skilled in the art (for example *Greene's Protective Groups in Organic Synthesis, 4th Edition*). Commercially available enantiomerically pure epoxides could be used to give single enantiomer products G9.

Scheme 2A

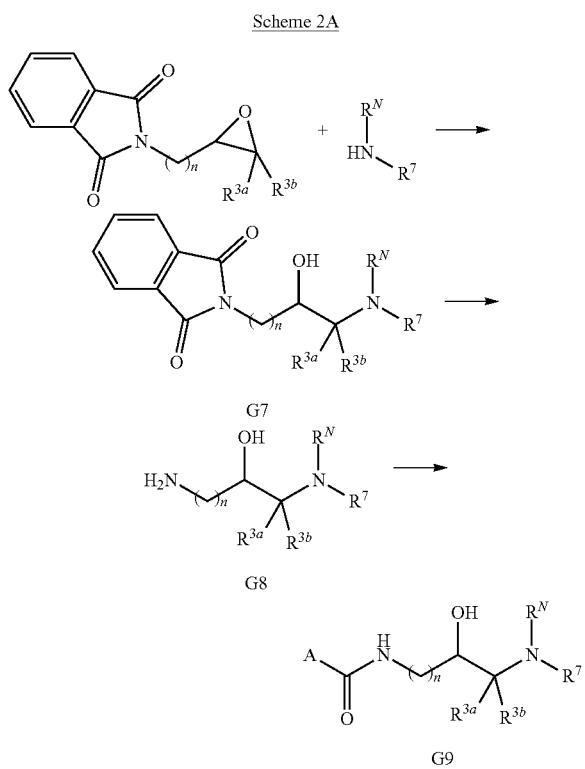

The amide formation to form G9 can be achieved by the methods outline in Scheme 1A. The synthesis of either enantiomer and the racemate can be achieved by the same method.

General Synthesis Method 3

Scheme 3A

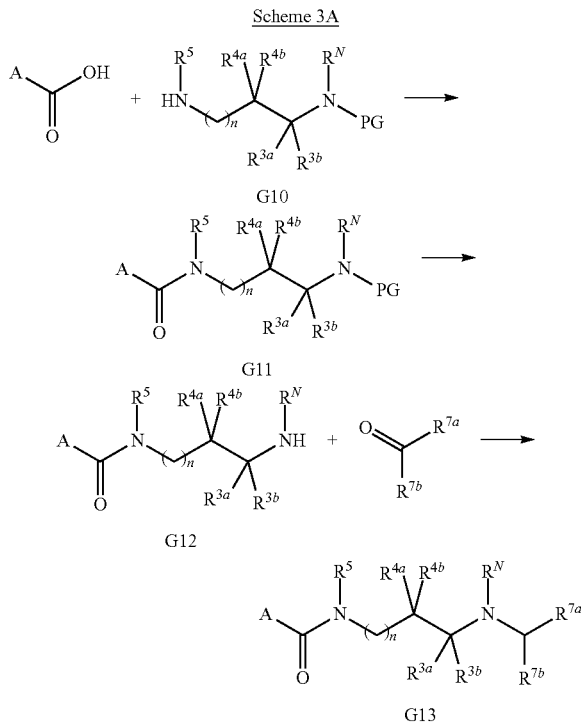

Where $R^{7a}$ and $R^{7b}$ together with the atom to which they are bound form $R^7$.

Scheme 3A illustrates the synthesis of compounds with the formula G13, beginning with an amide bond formation by coupling a relevant carboxylic acid to a primary amine or a secondary amine G10. Methods to form such amides will be apparent to those skilled in the art, but include for example the use of reagents such as HATU, HBTU, T3P and EDCI/HOBt, and the use of activated forms of the carboxylic acid such as the corresponding acyl halide, mixed anhydride or N-hydroxysuccinimide ester.

Suitably protected amino groups and methods for the removal of said protecting groups will be known to those skilled in the art (for example *Greene's Protective Groups in Organic Synthesis, 4th Edition*). Suitable protecting groups might include Boc, CBz, or phthalimide. Upon removal of the protecting group to provide compounds of the general formula G12, these intermediates can be converted to the desired compound, G13. Methods to form such an intermediate will be apparent to those skilled in the art, but include for example reductive amination by the use of reagents such as, but not limited to sodium triacetoxyborohydride or sodium cyanoborohydride with acetic acid, and sodium triacetoxyborohydride triacetoxyborohydride or sodium borohydride with $Ti(O^iPr)_4$.

General Synthesis Method 4

Scheme 4A

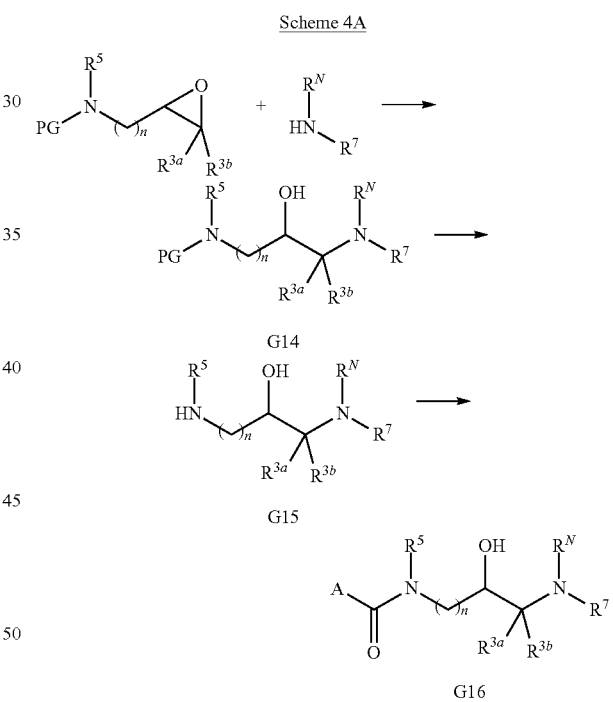

Scheme 4A illustrates an approach to the synthesis of compounds with the formula of G16, beginning with the reaction of the desired amine ($HNR^NR^7$) with an epoxide bearing a suitable protected amino group such as for example tert-butyl N-(oxiran-2-yl methyl) carbamate. Opening of the epoxide under suitable conditions furnishes the intermediate compound G14. Suitably protected amino groups and methods for the removal of said protecting groups will be known to those skilled in the art (for example *Greene's Protective Groups in Organic Synthesis, 4th Edition*). Upon removal of the protecting group to provide compounds of the general formula G15, these intermediates can be converted to the desired compound, G16, by the procedure outlined in Scheme 1A.

General Synthesis Method 5

Scheme 5A illustrates how to form amine substitutions such as shown in G17. An amide is reacted with a halo-epoxide or similar and the resultant mixture reacted on with a desired amine (HNR$^6$R$^7$) resulting in a product within the scope of G17. The group denoted (X) can be but is not limited to halogen, tosylate, nosylate or similar.

Scheme 5A

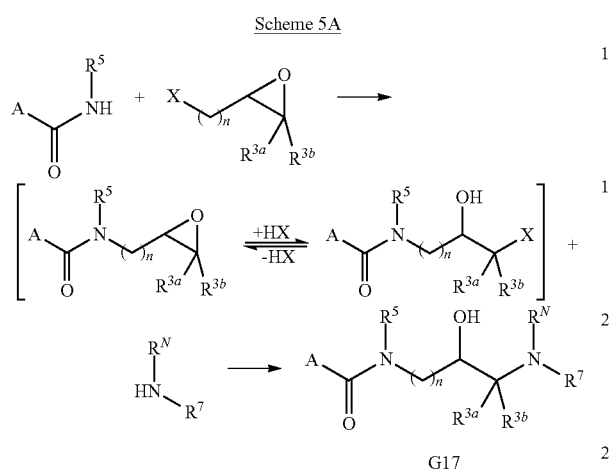

G17

Alternatively enantiomerically pure forms of the epoxide, e.g. epichlorohydrin, can be used to obtain the products G17 in enantiomerically pure form.

General Synthesis Method 6

Scheme 6A illustrates how to form amine substitutions such as shown in G19. Suitable amide protecting groups and methods for the removal of said protecting groups will be known to those skilled in the art (for example *Greene's Protective Groups in Organic Synthesis, 4th Edition*). An amide is reacted with a halo-epoxide or similar and the resultant mixture reacted on with a desired amine (HNR$^N$R$^7$) resulting in an intermediate G18. The group denoted (X) can be but is not limited to halogen, tosylate, nosylate or similar. Removal of the protecting group provides compounds of the general formula G19

Scheme 6A

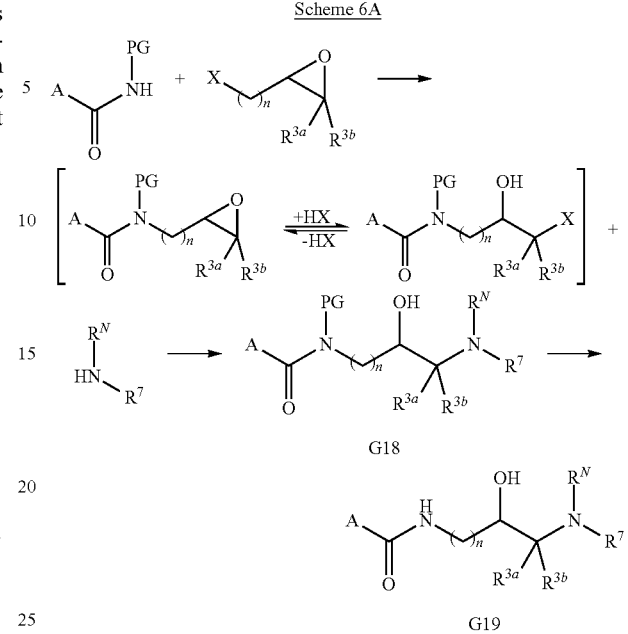

G18

G19

Alternatively enantiomerically pure forms of the epoxide for example include but are not limited to epichlorohydrin, can be used to obtain the products G14 in enantiomerically pure form.

General Synthesis Method 7

Scheme 7A illustrates an approach to the synthesis of compounds with the formula of G23, beginning with the reaction of the desired amine (HNR$^N$R$^7$) with an epoxide bearing a leaving group (LG). The group represented by (LG) includes but not limited to halide, mesylate, tosylate, nosylate. Depending on the conditions and the nature of the leaving group, the reaction can proceed through two different pathways to give either epoxide with structure G20 or alcohol with structure G21. Treatment of either compound with primary amine (R$^5$—NH$_2$) furnishes intermediates with structure G22. These intermediates can be converted to the desired compound, G23, by the procedure outlined in Scheme 1A.

Scheme 7a

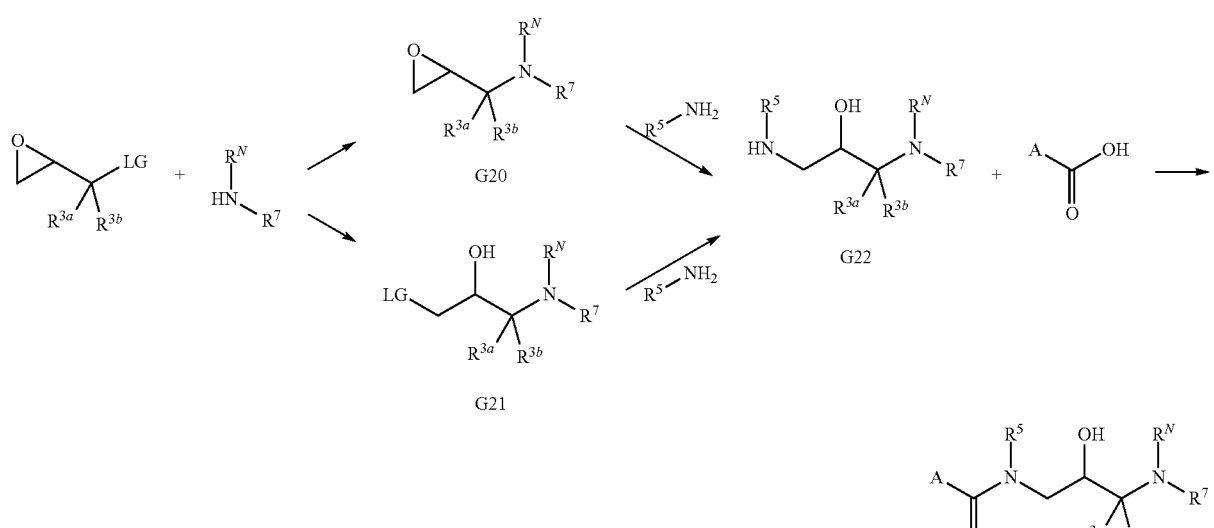

G20

G21

G22

G23

General Synthesis Method 8

Scheme 8A illustrates the synthesis of compounds G27 which begins with a coupling of a compound G24 with a desired amine (HNR$^N$R$^7$) by substitution of a leaving group (LG) to give intermediates G25. The group represented by (LG) includes but is not limited to halide, mesylate, tosylate, nosylate. The group represented by (PG) is a suitable amine protecting group which includes but is not limited to Boc, phthalimide, benzyl, PMB, allyl. Suitable amine protecting groups and methods for the removal of said protecting groups will be known to those skilled in the art (for example *Greene's Protective Groups in Organic Synthesis, 4th Edition*). Upon removal of the protecting group, coupling with a suitable carboxylic acid can be performed by methods illustrated in Scheme 1A.

Alternatively, as shown in Scheme 8B, compounds with structure G28 can be coupled with the desired amine (HNR$^N$R$^7$) to give compounds G27.

General Synthesis Method 9

Scheme 9A illustrates the synthesis of compounds G32 where R$^{3a}$ and R$^{3b}$ are hydrogen. Amide bond formation of compounds with structure G28 with the desired amine (HNR$^N$R$^7$) give compounds with structure G29. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. Reduction of the amide to the corresponding amine G30 will be apparent to those skilled in the art but such methods include but are not limited to the use of a reducing agent such as LiAlH$_4$. Suitable amine protecting groups and methods for the removal of said protecting groups will be known to those skilled in the art (for example *Greene's Protective Groups in Organic Synthesis, 4th Edition*). Upon deprotection, intermediates G31 can be converted to the desired compound, G32, by the procedure outlined in Scheme 1A.

Alternatively where X=H in G28, a reductive amination could be performed, for example using sodium triacetoxy borohydride and acetic acid to form G30 directly, rather than proceeding via intermediate G29.

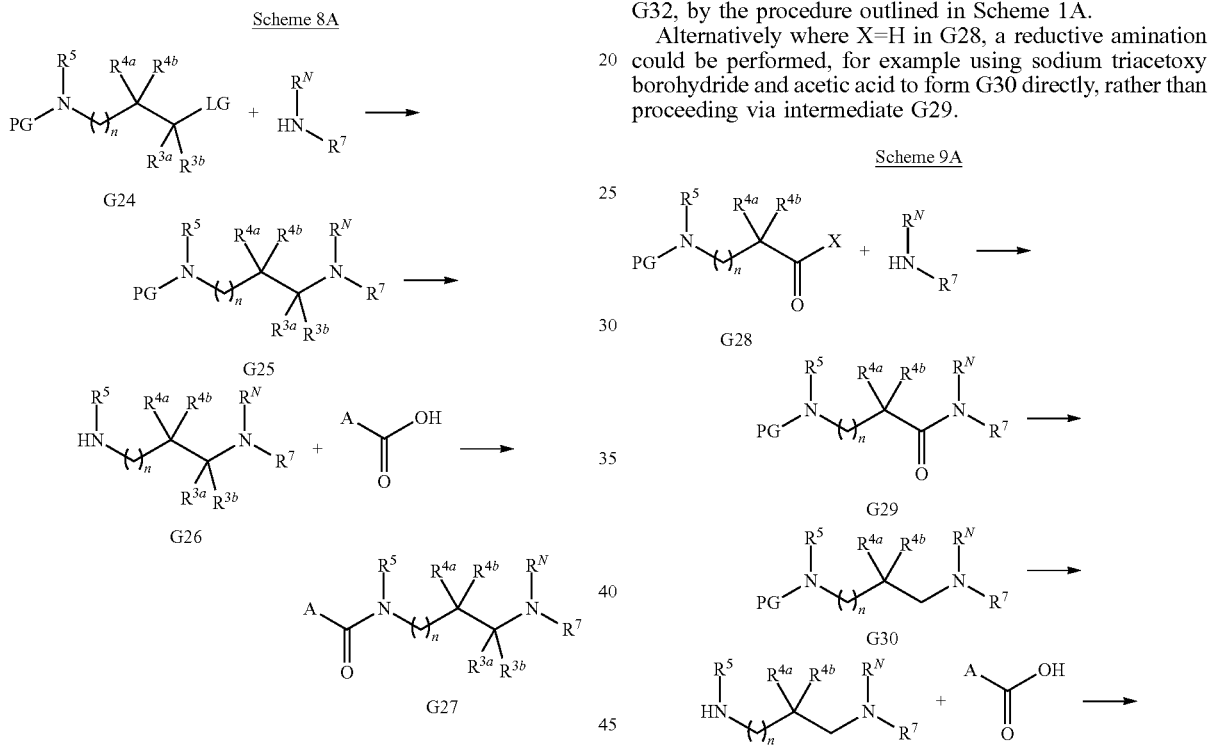

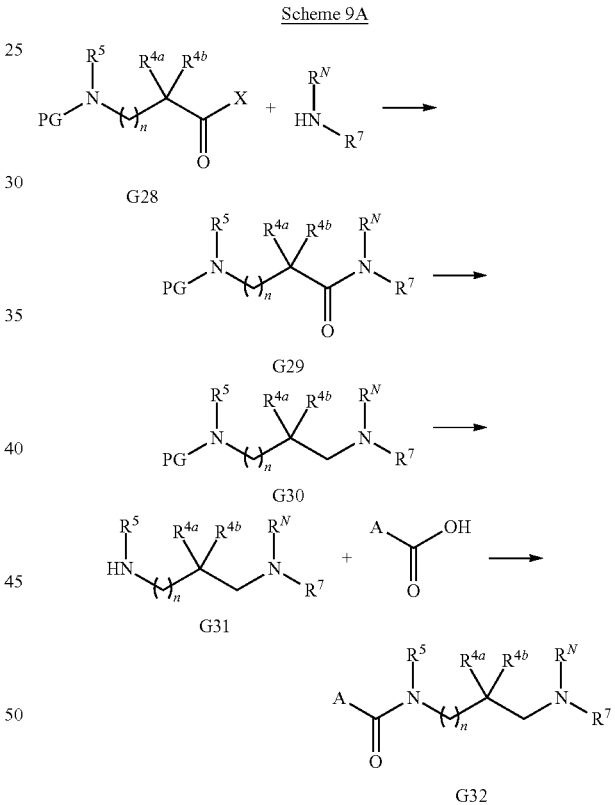

General Synthesis Method 10

Scheme 10A illustrates the addition of an amine (HNR$^8$R$^9$) as a substituent which is a part of A. This can be achieved by coupling a relevant carboxylic acid to a primary amine or a secondary amine, NHR$^8$R$^9$. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. The group denoted by (X) may be but not limited to halogen, tosylate or other suitable group. Conversion of (X) in G33 into an ester in G34 will be apparent to those skilled in the art, but include for example a carbonylation reaction which can be achieve by the use of carbon monoxide in the presence of an transition metal catalyst such as but not limited to PdCl$_2$dppf.DCM; and an alcoholic solvent such as but not limited to methanol, ethanol, isopropanol or tert-butyl alcohol. Formation of the carboxylic acid can be achieved by for example hydrolysis with a base such as an alkali metal hydroxide or an acid for example aqueous hydrochloric acid to form G35. The amide formation to form G36 can be achieved by the methods outline in Scheme 1A.

Scheme 10A

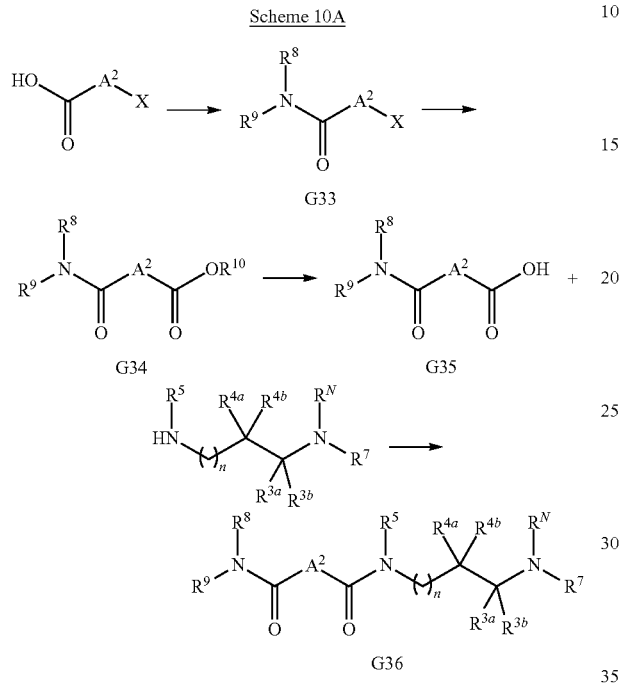

Alternatively, for the synthesis of ester G34 the order of steps can be reversed as described in Scheme 10B.

Scheme 10B

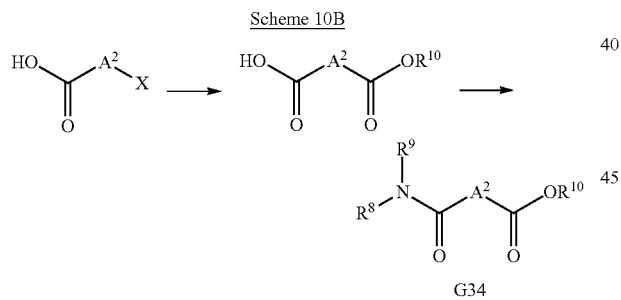

Alternatively for the synthesis of amide G36 the steps may be reordered such that the formation of the R$^8$R$^9$N amide on the A substituent occurs after the coupling of A to the amine G26. This may be achieved by coupling a suitable amine with an intermediate where A bears a suitable functional group for coupling, for example but not limited to a carboxylic acid or alkali metal carboxylate salt, as shown in Scheme 10C Scheme 10C

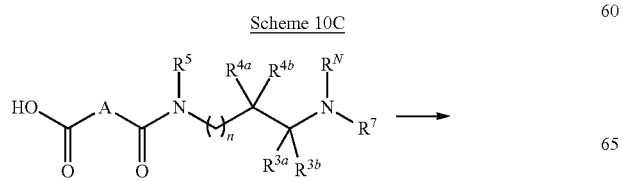

-continued

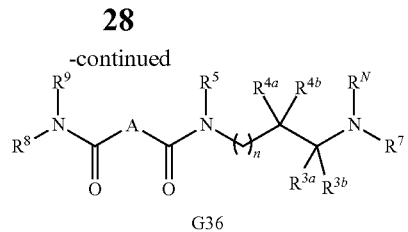

G36

Compounds of Formula Id

Compounds of formula Id, as described above, can be prepared by synthetic strategies outlined below, wherein the definitions above apply.

General Synthesis 11

Scheme 11A

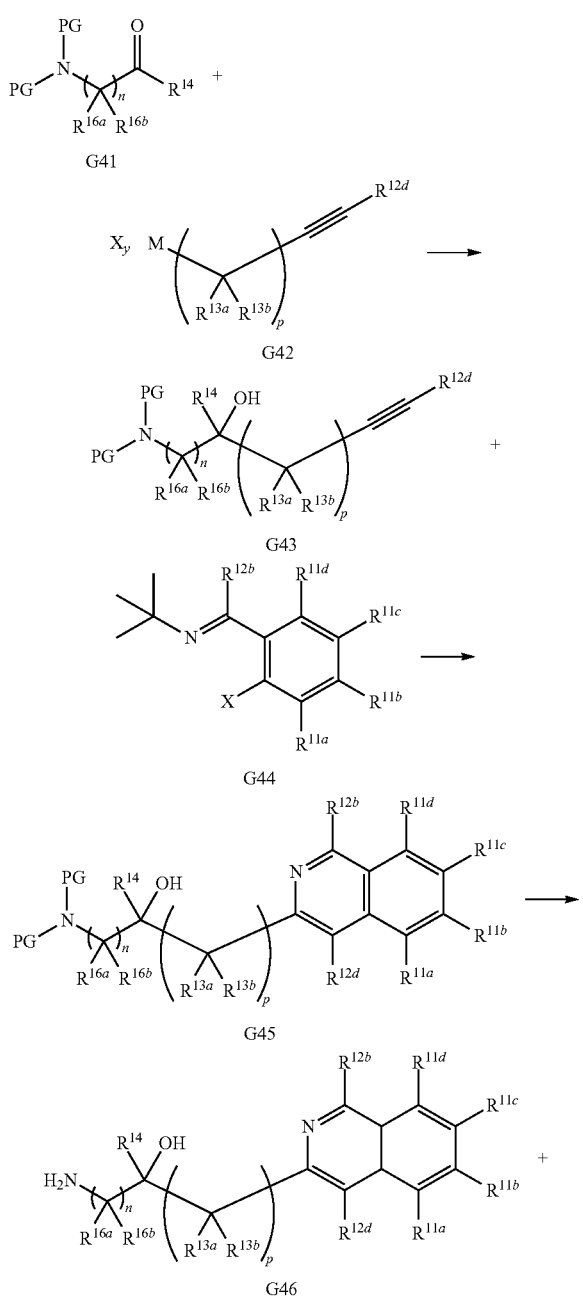

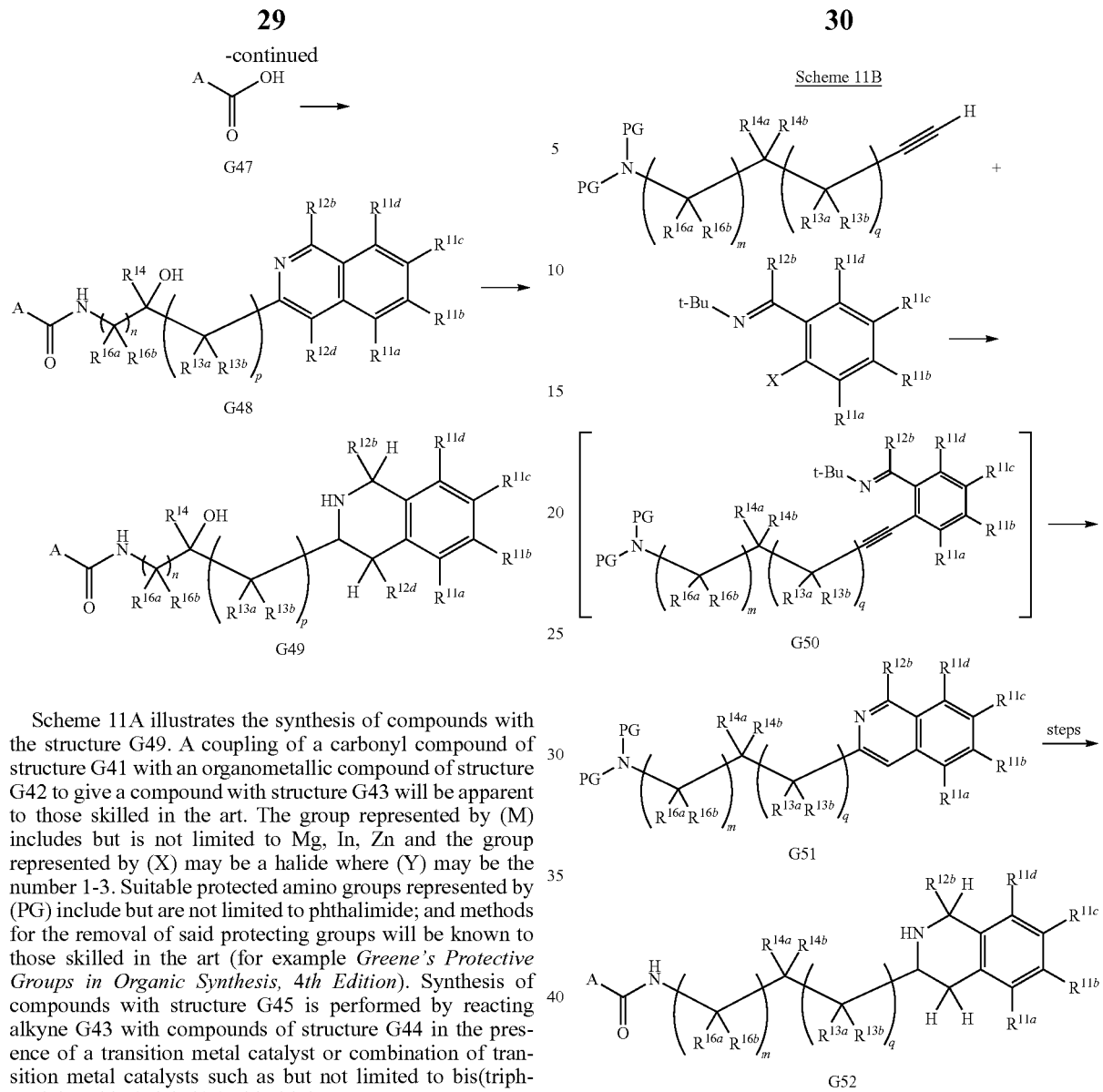

Scheme 11A illustrates the synthesis of compounds with the structure G49. A coupling of a carbonyl compound of structure G41 with an organometallic compound of structure G42 to give a compound with structure G43 will be apparent to those skilled in the art. The group represented by (M) includes but is not limited to Mg, In, Zn and the group represented by (X) may be a halide where (Y) may be the number 1-3. Suitable protected amino groups represented by (PG) include but are not limited to phthalimide; and methods for the removal of said protecting groups will be known to those skilled in the art (for example *Greene's Protective Groups in Organic Synthesis, 4th Edition*). Synthesis of compounds with structure G45 is performed by reacting alkyne G43 with compounds of structure G44 in the presence of a transition metal catalyst or combination of transition metal catalysts such as but not limited to bis(triphenylphosphine)nickel(II) chloride/Zn.

After removal of the protecting group, methods to synthesise amides G48 will be apparent to those skilled in the art, but include for example the use of reagents such as HATU, HBTU, T3P and EDCl/HOBt, and the use of activated forms of the carboxylic acid G47 such as the corresponding acyl halide, carbamate or N-hydroxysuccinimide ester. Transformation of isoquinolines of structure G48 to give tetrahydroisoquinolines of structure G49 will be apparent to those skilled in the art and such methods include but are not limited to reduction in the presence of a transition metal catalyst.

Alternatively, for the synthesis of compounds with structure G52 where $R^{2a}$, $R^{2b}$, $R^{2d}$=H, a coupling of an alkyne and a aryl halide will be apparent to those skilled in the art and such methods include a coupling in the presence of a transition metal catalyst or catalyst combination such as but not limited to $PdCl_2(PPh_3)_2$/CuI and $Pd(OAc)_2$/$PPh_3$. This may be followed by cyclisation either in situ or as a separate step to give isoquinoline of structure G51. The synthetic steps to give compounds with general formula G52 will be similar to those used in Scheme 11A.

General Synthesis 12

Scheme 12A

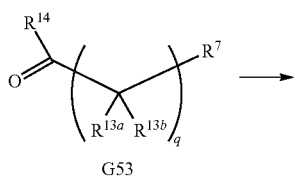

G53

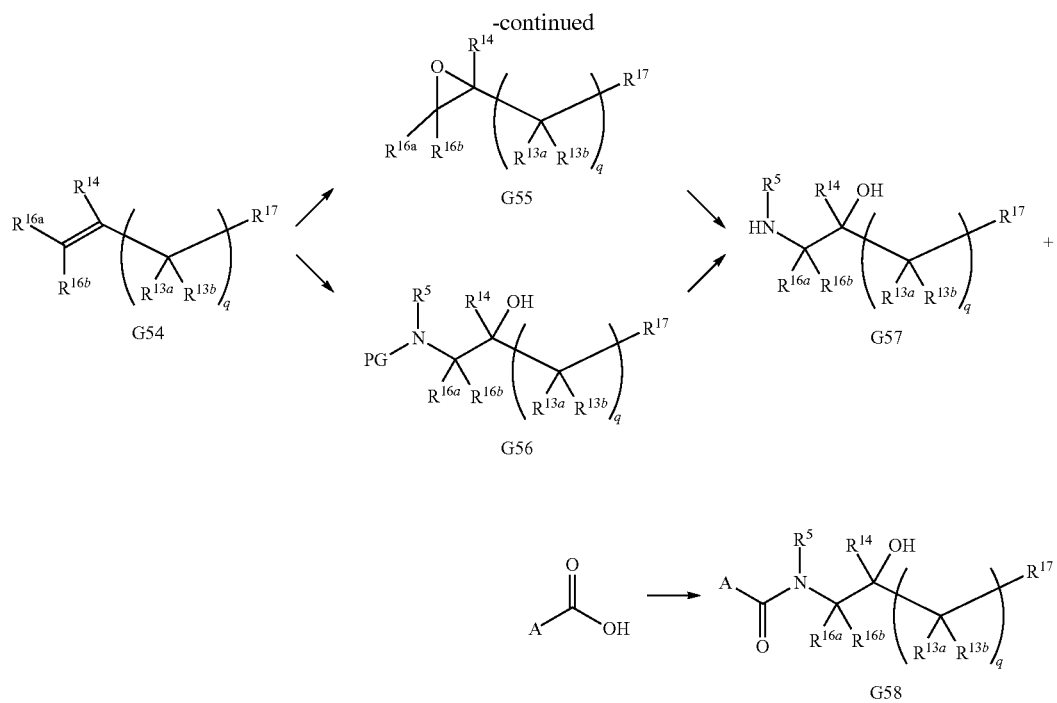

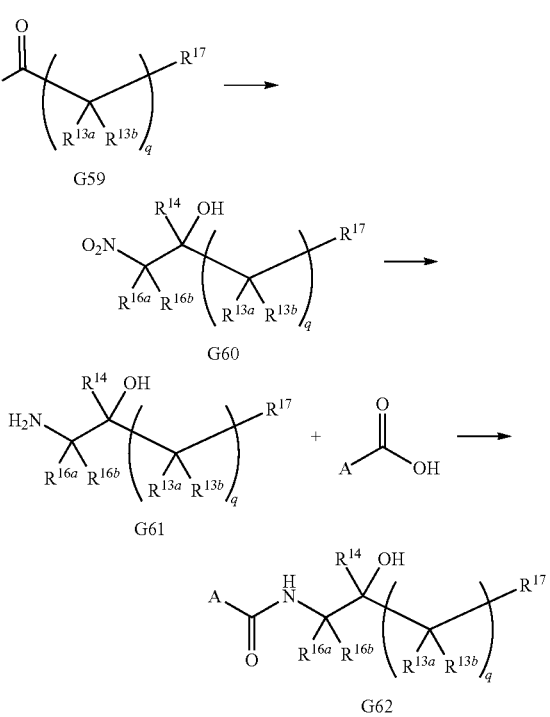

Where $R^{17}$ represents the fused ring group.

Scheme 12A illustrates the synthesis of compounds G58 from aldehyde G53 (or ketone where $R^{14}$=Me). Conversion of a carbonyl to an alkene will be apparent to those skilled in the art but methods include but are not limited to a Wittig reaction with [Ph$_3$PMe]$^+$Br$^-$ in the presence of a base such as KHMDS. The alkene G54 can be epoxidised with reagents such as mCPBA and then reacted with an amine to give intermediate G57. Alternatively, an aminohydroxylation can be performed by methods such as but not limited to reaction with (PG)NHOTs in the presence of potassium osmate dihydrate to give G56. Removal of the protecting group will be apparent to those skilled in the art (for example *Greene's Protective Groups in Organic Synthesis, 4th Edition*) and gives intermediate G57. Amide bond formation to give compounds G58 can be performed by methods previously described (General synthesis 11).

General Synthesis 13

Scheme 13A illustrates the synthesis of compounds G62 beginning with a Henry reaction between an aldehyde G59 (or ketone where $R^{14}$=Me) and nitromethane in the presence or absence of a suitable base, such as but not limited to DBU, a KF, TBAF or sodium hydroxide, in the presence or absence of a chiral or achiral transition metal compound for example but not limited to complexes of copper, cobalt or zinc to furnish a nitro-alcohol G60. Reduction of the nitro group to the primary amine G61 will be apparent to those skilled in the art and include but are not limited to using reducing conditions such as a transition metal (Fe, In, Zn) in the presence of HCl, hydrogenation in the presence of a transition metal or transition metal catalyst. Amide bond formation to give compounds G62 can be performed by methods previously described (General synthesis 11). The method can also be carried out with nitroethane and other nitroalkanes, as appropriate.

Scheme 13A

General Synthesis 14

Scheme 14A illustrates the addition of an amine (HNR$^8$R$^9$), as a substituent which is a part of A. This can be achieved by coupling a relevant carboxylic acid to a primary amine or a secondary amine, NHR$^8$R$^9$. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. The group denoted by (X) may be but not limited to halogen, tosylate or other suitable group. Conversion of (X) in G62 into an ester in G63 will be apparent to those skilled in the art, but include for example a carbonylation reaction which can be achieved by the use of carbon monoxide in the presence of an transition metal catalyst such as but not limited to $PdCl_2$dppf.DCM; and an alcoholic solvent such as but not limited to methanol, ethanol, isopropanol or tert-butyl alcohol. Formation of the carboxylic acid can be achieved by for example hydrolysis with a base such as an alkali metal hydroxide or an acid for example aqueous hydrochloric acid to form G64. The amide formation to form G65 can be achieved by the methods outline in Scheme 11A.

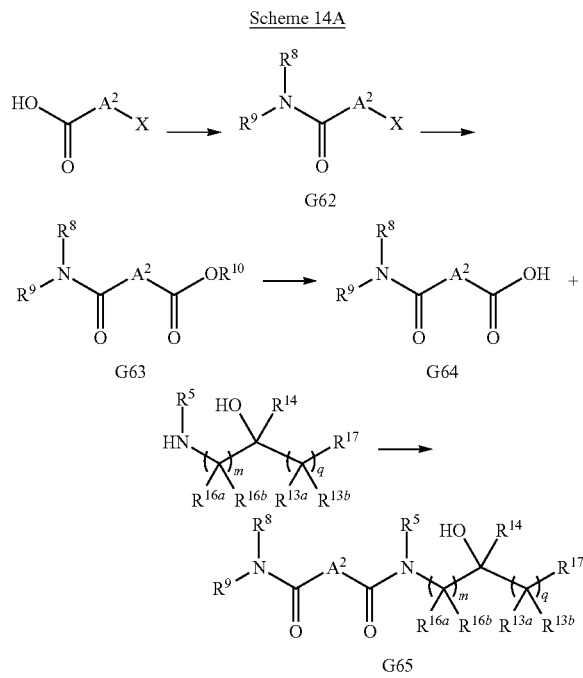

Alternatively, for the synthesis of ester G63 the order of steps can be reversed as described in Scheme 14B.

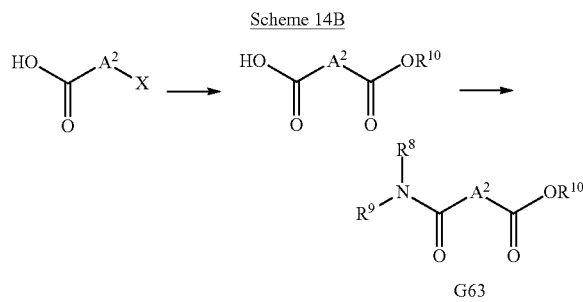

Alternatively for the synthesis of amide G65 the steps may be reordered such that the formation of the $R^8R^9N$ amide on the A substituent occurs after the coupling of A to the primary amine G61. This may be achieved by coupling a suitable amine with an intermediate where A bears a suitable functional group for coupling, for example but not limited to a carboxylic acid or alkali metal carboxylate salt, as shown in Scheme 14C.

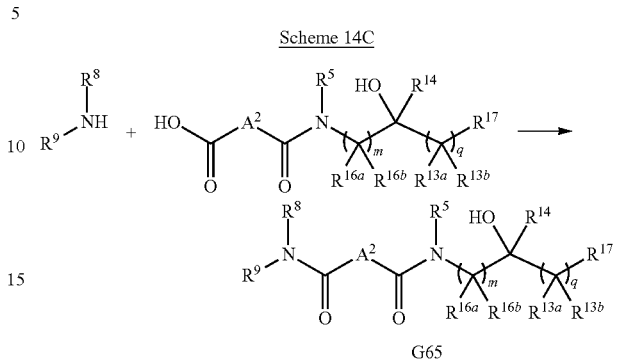

FURTHER EMBODIMENTS n

In some embodiments, n is 1. In some embodiments, n is 2.

$R^N$

In some embodiment, $R^N$ is H. In other embodiments, $R^N$ is Me.

$R^1$

In some embodiments, there may be no $R^1$ substituents. In some embodiments, $R^1$ represents one to four Me or halo groups, preferably one to three Me or halo groups and more preferably one or two Me or halo groups. In some of these embodiments, $R^1$ may represent F. In others of these embodiments, $R^1$ may represent Me groups.

$R^2$ $R^{2a}$, $R^{2b}$, $R^{2c}$ and $R^{2d}$ (if present) are independently selected from H, F, $CH_2OH$ and Me. In some of these embodiments, $R^{2a}$, $R^{2b}$, $R^{2c}$ and $R^{2d}$ (if present) are independently selected from H, Me and $CH_2OH$. In further of these embodiments, $R^{2a}$, $R^{2b}$, $R^{2c}$ and $R^{2d}$ (if present) are independently selected from H and Me.

In some embodiments $R^{2a}$, $R^{2b}$, $R^{2c}$ and $R^{2d}$ (if present) are all H.

In some of those embodiments where $R^{2a}$, $R^{2b}$, $R^{2c}$ and $R^{2d}$ are all present (i.e. formulae Ia and Ib), they may be comprised of three H and one Me or $CH_2OH$ group. It may be preferred in these embodiments that $R^{2a}$ is Me and $R^{2b}$, $R^{2c}$ and $R^{2d}$ are H. It may be preferred in these embodiments that $R^{2c}$ is Me or $CH_2OH$ and $R^{2a}$, $R^{2b}$ and $R^{2d}$ are H.

In some of those embodiments where $R^{2a}$, $R^{2b}$, $R^{2c}$ and $R^{2d}$ are all present (i.e. formulae Ia and Ib), they may be comprised of two H and two Me groups. It may be preferred in these embodiments that $R^{2a}$ and $R^{2c}$ are Me and $R^{2b}$ and $R^{2d}$ are H. It may be preferred in these embodiments that $R^{2a}$ and $R^{2b}$ are Me and $R^{2c}$ and $R^{2d}$ are H. It may also be preferred in these embodiments that $R^{2c}$ and $R^{2d}$ are Me and $R^{2a}$ and $R^{2b}$ are H.

In some of those embodiment where only $R^{2a}$ and $R^{2b}$ are present (i.e. formula Ic), they may be comprised of one H and one Me or $CH_2OH$ group.

In some of those embodiment where only $R^{2a}$ and $R^{2b}$ are present (i.e. formula Ic), they may both be a Me or $CH_2OH$ group.

R³

R$^{3a}$ and R$^{3b}$ are independently selected from H and Me. In some embodiments R$^{3a}$ is H and R$^{3b}$ is Me. In some embodiments R$^{3a}$ and R$^{3b}$ are both H. In some embodiments R$^{3a}$ and R$^{3b}$ are both Me.

R$^{4a}$

In some embodiments R$^{4a}$ is OH.

In other embodiments, R$^{4a}$ is —NH$_2$. In other embodiments R$^{4a}$ is —C(=O)NH$_2$. In other embodiments R$^{4a}$ is —CH$_2$OH.

It may be preferred that R$^{4a}$ is OH.

R$^{4b}$

In some embodiments R$^{4b}$ is H. In some embodiments R$^{4b}$ is Me.

R$^5$

In some embodiments R$^5$ is H. In some embodiments R$^5$ is Me.

Enantiomers

The carbon to which R$^{4a}$ and R$^{4b}$ are attached is a chiral centre.

When the compound contains this chiral centre, in some embodiments, the compound is a racemate.

When the compound contains this chiral centre, in some embodiments, the compound is a single enantiomer. In some of these embodiments, the compound is the (R)-enantiomer. In others of these embodiments, the compound is the (S)-enantiomer.

The compound may also include further chiral centres, for example, in compounds of formula Ia, in tetrahydronaphthalenyl group. In some embodiments, the compound is a racemate. In other embodiments, the compound is a single enantiomer. In some of these embodiments, the compound is the (R)-enantiomer. In others of these embodiments, the compound is the (S)-enantiomer.

R$^1$-R$^5$ & n

In some embodiments, R$^N$, R$^1$, R$^{2a}$, R$^{2b}$, R$^{2c}$ (if present), R$^{2d}$ (if present), R$^{3a}$, R$^{3b}$, R$^{4b}$ and R$^5$ are all H, R$^{4a}$ is OH and n is 1, and thus the compound of formula Ia is of formula Ia1, the compound of formula Ib is of formula Ib1, and the compound of formula Ic is of formula Id:

(Ia1)
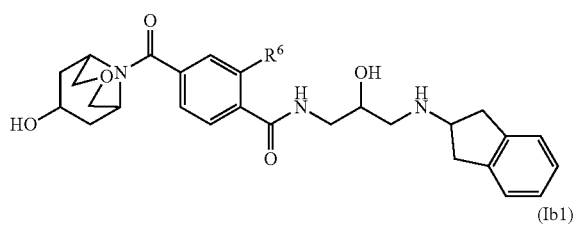

(Ib1)
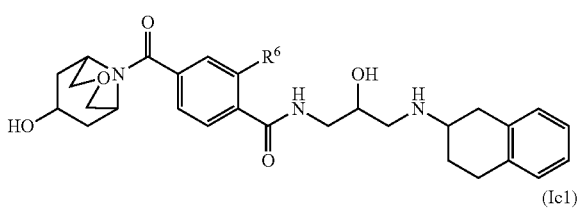

(Ic1)
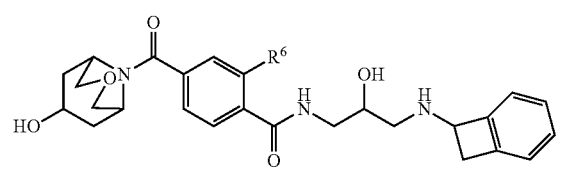

In some embodiments, R$^1$, R$^{2a}$, R$^{2b}$, R$^{2c}$ (if present), R$^{2d}$ (if present), R$^{3a}$, R$^{3b}$, R$^{4b}$ and R$^5$ are all H, R$^{4a}$ is OH and n is 2, and thus the compound of formula Ia is of formula Ia2, the compound of formula Ib is of formula Ib2, and the compound of formula Ic is of formula Ic2:

(Ia2)
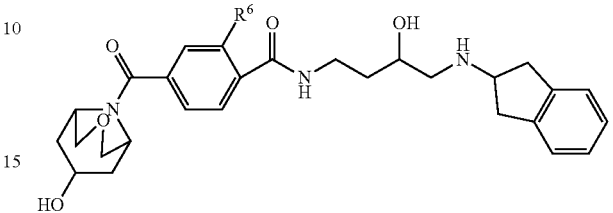

(Ib2)
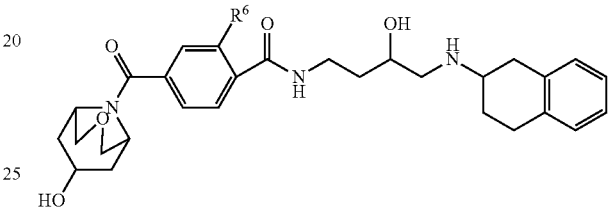

(Ic2)
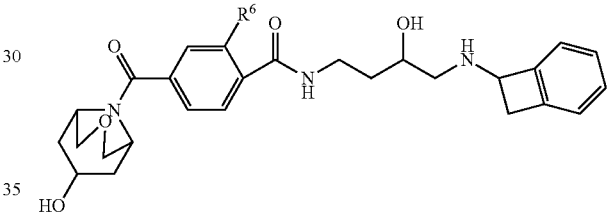

m

In some embodiments, m is 1. In some embodiments, m is 2.

q

In some embodiments, q is 0. In some embodiments, q is 1.

R$^{11a}$, R$^{11b}$, R$^{11c}$ and R$^{11d}$

In some embodiments, R$^{11a}$, R$^{11b}$, R$^{11c}$ and R$^{11d}$ are all H.

In some embodiments, one of R$^{11a}$, R$^{11b}$, R$^{11c}$ and R$^{11d}$ is C$_{1-4}$ alkoxy, C$_{1-4}$ alkyl, C$_{1-4}$ fluoroalkyl, C$_{3-4}$ cycloalkyl, NH—C$_{1-4}$ alkyl, halo or cyano. In some of there embodiments, R$^{11b}$ or R$^{11c}$ is C$_{1-4}$ alkoxy, C$_{1-4}$ alkyl, C$_{1-4}$ fluoroalkyl, C$_{3-4}$ cycloalkyl, NH—C$_{1-4}$ alkyl, halo or cyano, and in further of these embodiments, R$^{11b}$ is C$_{1-4}$ alkoxy, C$_{1-4}$ alkyl, C$_{1-4}$ fluoroalkyl, C$_{3-4}$ cycloalkyl, NH—C$_{1-4}$ alkyl, halo or cyano. Where one of R$^{11a}$, R$^{11b}$, R$^{11c}$ and R$^{11d}$ is C$_{1-4}$ alkoxy, C$_{1-4}$ alkyl, C$_{1-4}$ fluoroalkyl, C$_{3-4}$ cycloalkyl, NH—CH$_{1-4}$ alkyl, halo or cyano, it may be that the group is methoxy, methyl, NHMe, F or cyano. In some embodiments, the group is methoxy.

R12

R$^{12a}$, R$^{12b}$, R$^{12c}$ and R$^{12d}$ are independently selected from H, F, CH$_2$OH and Me. In some of these embodiments, R$^{12a}$, R$^{12b}$, R$^{12c}$ and R$^{12d}$ are independently selected from H, Me and CH$_2$OH. In further of these embodiments, R$^{12a}$, R$^{12b}$, R$^{12c}$ and R$^{12d}$ are independently selected from H and Me.

In some embodiments R$^{12a}$, R$^{12b}$, R$^{12c}$ and R$^{12d}$ are all H.

In some embodiments R$^{12a}$, R$^{12b}$, R$^{12c}$ and R$^{12d}$ are comprised of three H and one Me or CH$_2$OH group. It may be preferred in these embodiments that R$^{12a}$ is Me and R$^{12b}$, $R^{12c}$ and $R^{12d}$ are H. It may be preferred in these embodiments that $R^{12c}$ is Me or $CH_2OH$ and $R^{12a}$, $R^{12b}$ and $R^{12d}$ are H.

In some embodiments $R^{12a}$, $R^{12b}$, $R^{12c}$ and $R^{12d}$ are comprised of two H and two Me groups. It may be preferred in these embodiments that $R^{12a}$ and $R^{12c}$ are Me and $R^{12b}$ and $R^{12d}$ are H. It may be preferred in these embodiments that $R^{12a}$ and $R^{12b}$ are Me and $R^{12c}$ and $R^{12d}$ are H. It may also be preferred in these embodiments that $R^{12c}$ and $R^{12d}$ are Me and $R^{12a}$ and $R^{12b}$ are H.

In some embodiments, $R^{12c}$ and $R^{12d}$ are independently selected from H and F.

$R^{12e}$

In some embodiments, Rue is H. In other embodiments, Rue is Me.

$R^{13}$ $R^{13a}$ and $R^{13b}$ are independently selected from H and Me. In some embodiments $R^{13a}$ is H and $R^{13b}$ is Me. In some embodiments $R^{13a}$ and $R^{13b}$ are both H. In some embodiments $R^{13a}$ and $R^{13b}$ are both Me.

$R^{14}$

In some embodiments $R^{14}$ is H. In some embodiments $R^{14}$ is Me.

$R^{16}$ $R^{16a}$ and $R^{16b}$ are independently selected from H and Me. In some embodiments $R^{16a}$ is H and $R^{16b}$ is Me. In some embodiments $R^{16a}$ and $R^{16b}$ are both H. In some embodiments $R^{16a}$ and $R^{16b}$ are both Me.

Stereoisomers

The carbon to which $R^{14}$ is attached is a chiral centre.

In some embodiments, the compound is a mixture of stereoisomers at this centre. In some embodiments, the compound is a single stereoisomer. In some of these embodiments, the compound is the (R)-stereoisomer. In others of these embodiments, the compound is the (S)-stereoisomer.

The compound may also include further chiral centres. The carbon in the THIQ moiety is chiral. In some embodiments, the compound is a mixture of stereoisomers at this centre. In other embodiments, the compound is a single stereoisomer at this centre. In some of these embodiments, the compound is the (R)-stereoisomer at this centre. In others of these embodiments, the compound is the (S)-stereoisomer at this centre.

Thus the compound may be a single diastereomer or a mixture of diastereomers.

It may be preferred the compounds have the following stereochemistry:

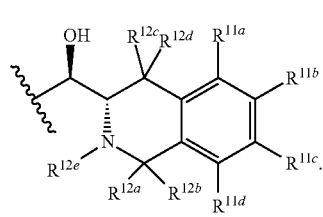

Alternatively, the compounds may have one of the following stereochemistries:

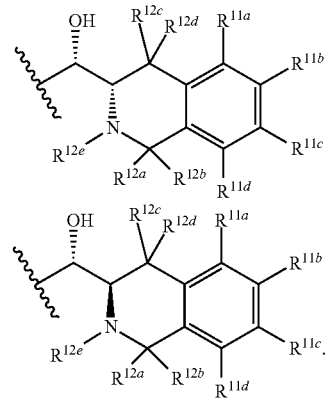

Furthermore, the compounds may have the following stereochemistry:

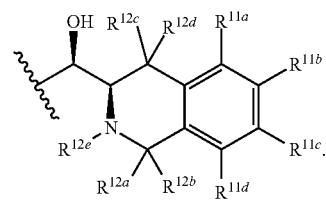

$R^{11}$-$R^{15}$ n & p

In some embodiments, $R^{11a}$, $R^{11b}$, $R^{11c}$, $R^{11d}$, $R^{12a}$, $R^{12b}$, $R^{12c}$, $R^{12d}$, $R^{12e}$, $R^{14}$, $R^{15}$, $R^{16a}$ and $R^{16b}$ are all H, n is 1 and p is 0, and thus the compound of formula I is of formula Id1:

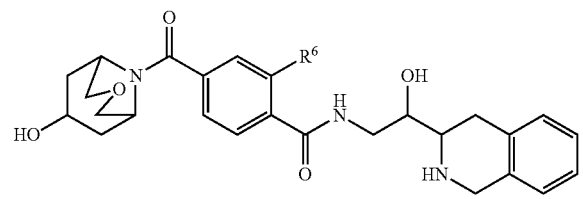

(Id1)

In some embodiments, $R^{11a}$, $R^{11b}$, $R^{11c}$, $R^{11d}$, $R^{12a}$, $R^{12b}$, $R^{12c}$, $R^{12d}$, $R^{12e}$, $R^{13a}$, $R^{13b}$, $R^{14}$, $R^{15}$, $R^{16a}$ and $R^{16b}$ are all H, n is 1 and p is 1, and thus the compound of formula I is of formula Id2:

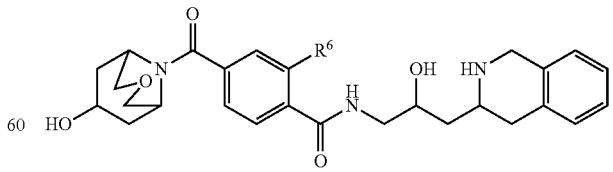

(Id2)

In some embodiments, $R^{11a}$, $R^{11b}$, $R^{11c}$, $R^{11d}$, $R^{12a}$, $R^{12b}$, $R^{12c}$, $R^{12d}$, $R^{12e}$, $R^{14}$, $R^{15}$, $R^{16a}$ are all H, n is 1 and p is 0, and $R^{16b}$ is Me and thus the compound of formula I is of formula Id3:

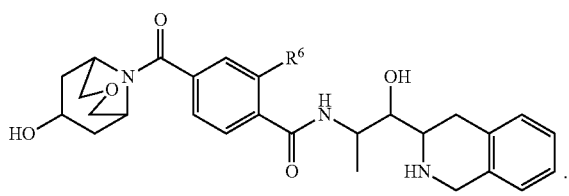

(Id3)

R⁶

In some embodiments, $R^6$ is H.
In some embodiments, $R^6$ is OMe.
In some embodiments, $R^6$ is OEt.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol (d₄-MeOD) ethanol (EtOH), isopropanol (i-PrOH), ether or diethyl ether (Et₂O), ethyl acetate (EtOAc), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), deuterated chloroform (CDCl₃), diethylamine (DEA), deuterated dimethylsulfoxide (d₆-DMSO), N-ethyl-N'-(3-dimethylaminopropyl)carbodiimide hydrochloride (EDCl.HCl, EDCl), meta-chloroperoxybenzoic acid (mCPBA), 1,1'-bis(diphenylphosphino)ferrocene (dppf), tert-butyloxycarbonyl (Boc, BOC), 2-(trimethylsilyl) ethoxymethyl (SEM), triethylamine (Et₃N or TEA), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA or DIEA), 1,1'-bis(diphenylphosphino)ferrocene dichloropalladium (II) (PdCl₂(dppf)), trans-dichlorobis(triphenylphosphine) palladium(II) (PdCl₂(PPh₃)₂), tris(dibenzylideneacetone) dipalladium(0) (Pd₂(dba)₃), tetrakis(triphenylphosphine) palladium(0) (Pd(PPh₃)₄), propylphosphonic anhydride (T3P), hexamethylphosphoramide (HMPA), 1,2-dichloroethane (DCE), benzyl (Bn) and 1-hydroxybenzotriazole (HOBt).

In addition, TLC refers to thin layer chromatography.

General Experimental Details

Unless otherwise stated the following generalisations apply. ¹H NMR spectra were recorded on a Bruker Ultrashield Plus (400 MHz) or a Bruker AVANCE (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

LCMS data was generated using either an Agilent 6100 Series Single Quad LCMS (LCMS-A), an Agilent 1260 Infinity Series UPLC/MS (LCMS-B), an Agilent 1200 Series G6110A Quadrupole LCMS or Waters 2695 alliance (LCMS-C). Chlorine isotopes are reported as ³⁵Cl, Bromine isotopes are reported as either ⁷⁹Br or ⁸¹Br or both ⁷⁹Br/⁸¹Br.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC conditions:
Reverse Phase HPLC analysis
Column: Luna C₈ (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min LCMS Method C (LCMS-C):
Instrument: Agilent 1200 Series G6110A Quadrupole
Pump: Binary pump
Detector: DAD
LC conditions:
Reverse Phase HPLC analysis
Column: Xbridge-C18, 2.5 μm, 2.1×30 mm
Column temperature: 30° C.
Injection Volume: 1-10 μL
Solvent A: Water 0.07% Formic acid
Solvent B: Methanol
Gradient: 30-95% solvent B over 3.5 min (for medium polarity samples) or 10-95% solvent B over 3.7 min (for large polarity samples)

Detection: monitored at 254 nm and 214 nm
MS conditions:
Ion Source: Quadrupole
Ion Mode: ES+
Drying gas temp: 350° C.
Drying gas flow: 10 L/min
Nebulizer pressure: 35 psi
Capillary voltage (V): 3500 (positive)
Scan Range: 50-900
Or
Instrument: Waters 2695 alliance
Pump: Quaternary Pump
Detector: 2996 Photodiode Array Detector
MS model: Micromass ZQ
LC conditions:
Column: Xbridge-C18, 3.5 μm, 2.1×50 mm
Column temperature: 30° C.
Injection volume: 1-10 μL
Acquisition of wavelength: 214 nm, 254 nm
Solvent A: 0.07% HCOOH aqueous solution
Solvent B: MeOH
Run time: 8 min
Gradient: 20-95% solvent B over 5 min
Detection: 254 nm and 214 nm
MS condition:
Ion source: ES+(or ES−) MS range: 50-900 m/z
Capillary: 3 kV Cone: 3 V Extractor: 3 V
Drying gas flow: 600 L/hr cone: 50 L/hr
Desolvation temperature: 300° C.
Source temperature: 100° C.
Sample Preparation:
  The sample was dissolved in methanol, the concentration about 0.1-1.0 mg/mL, then filtered through the syringes filter with 0.22 μm.
Preparative RP-HPLC:
Agilent 1260 Infinity HPLC system
UV detection at 210 nm and 254 nm
Gradient or isocratic elution through a Phenomenex Luna C8 (2) column 100 Å Axia (250×21.2 mm; particle size 5 μm)
Flow rate: 10 mL/min
Gradients are as specified in the individual examples.
  Analytical thin-layer chromatography was performed on Merck silica gel 60 F254 aluminium-backed plates which were visualised using fluorescence quenching under UV light or a basic $KMnO_4$ dip or Ninhydrin dip.
  Preparative thin-layer chromatography (prep TLC) was performed using Tklst (China), grand grade: (HPTLC): 8±2 μm>80%; (TLC): 10-40 μm. Type: GF254. Compounds were visualised by UV (254 nm).
  Flash chromatography was performed using a Biotage Isolera purification system using either Grace or RediSep® silica cartridges.
  Column chromatography was performed using Tklst (China), grand grade, 100-200 meshes silica gel.
  Microwave irradiation was achieved using a CEM Explorer SP Microwave Reactor.
  Where necessary, anhydrous solvents were purchased from Sigma-Aldrich or dried using conventional methods. Solutions of inorganic acids or bases where made up as aqueous solutions unless stated otherwise.
  Additional Cartridges used are as follows:
Phase Separator:
  Manufacturer: Biotage
  Product: ISOLUTE Phase Separator (3 mL unless otherwise stated)

SCX and SCX-2 Cartridges:
  Manufacturer: Biotage
  Product: ISOLUTE SCX 1 g, (6 mL SPE Column unless otherwise stated)
  Manufacturer: Biotage
  Product: ISOLUTE SCX-2 1 g (6 mL Column)
  Manufacturer: Silicycle
  Product: SCX-2 500 mg or 5 g
  Manufacturer: Agilent
  Product: Bond Elute SCX 10 g
Sample Extraction Cartridge:
  Manufacturer: Waters
  Product: Oasis HLB 35 cc (6 g) LP extraction cartridge Intermediate Preparations (i) (R)-tert-Butyl(3-amino-2-hydroxypropyl)(2,3-dihydro-1H-inden-2-yl)carbamate (I2)

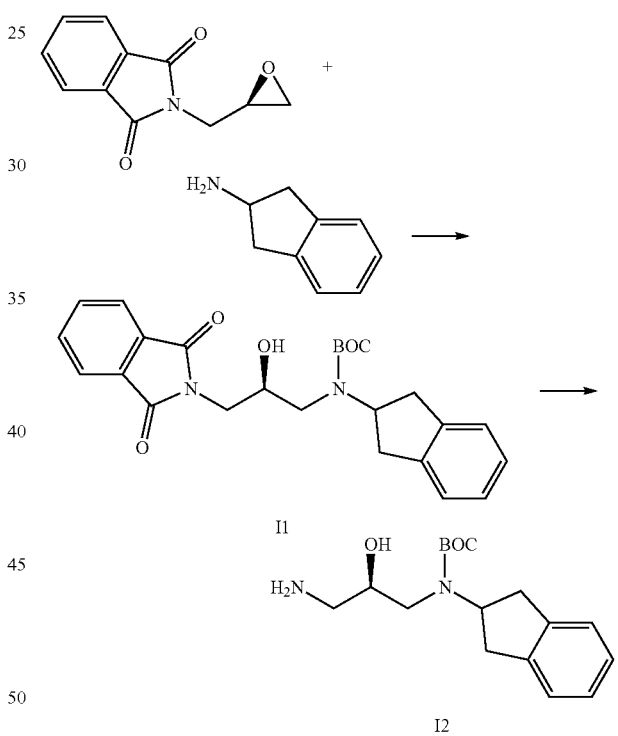

(a) (R)-tert-Butyl(2,3-dihydro-1H-inden-2-yl)(3-(1,3-dioxoisoindolin-2-yl)-2-hydroxypropyl)carbamate (I1)

A mixture of 2,3-dihydro-1H-inden-2-amine (5.0 g, 24.61 mmol) and (R)-2-(oxiran-2-ylmethyl)isoindoline-1,3-dione (4.91 g, 36.91 mmol) in EtOH (100 mL) was heated at reflux overnight. After cooling to room temperature, triethylamine (9.94 g, 98.44 mmol) and $(Boc)_2O$ (10.74 g, 49.22 mmol) were added and the reaction mixture was stirred at room temperature overnight. The mixture was concentrated and purified by column (EtOAc/petroleum ether=¼, v/v) to give the title compound (5.4 g, 50%) as an oil.

(b) (R)-tert-Butyl(3-amino-2-hydroxypropyl)(2,3-dihydro-1H-inden-2-yl)carbamate (I2)

A mixture of (R)-tert-butyl(2,3-dihydro-1H-inden-2-yl)(3-(1,3-dioxoisoindolin-2-yl)-2-hydroxypropyl)carbamate I1 (4.4 g, 10.08 mmol) and NH₂NH₂·H₂O (80%, 1.89 g, 30.24 mmol) in EtOH (100 mL) was heated at reflux for 4 hours. After cooling to room temperature, the mixture was filtered and the filtercake was washed with EtOH (50 mL). The filtrate was concentrated and then dissolved in CH₂Cl₂, washed with saturated aqueous NaHCO₃ solution (80 mL×3), brine (20 mL×2), dried (Na₂SO₄), filtered and concentrated to give the title compound (3.1 g, crude) as a yellow oil, which was used for the next step without further purification. LCMS: RT 2.17 min; m/z 307.2 [M+H]⁺.

(ii) (R)-4((3-((tert-Butoxycarbonyl)(2,3-dihydro-1H-inden-2-yl)amino)-2-hydroxypropyl)carbamoyl)-3-ethoxybenzoic acid

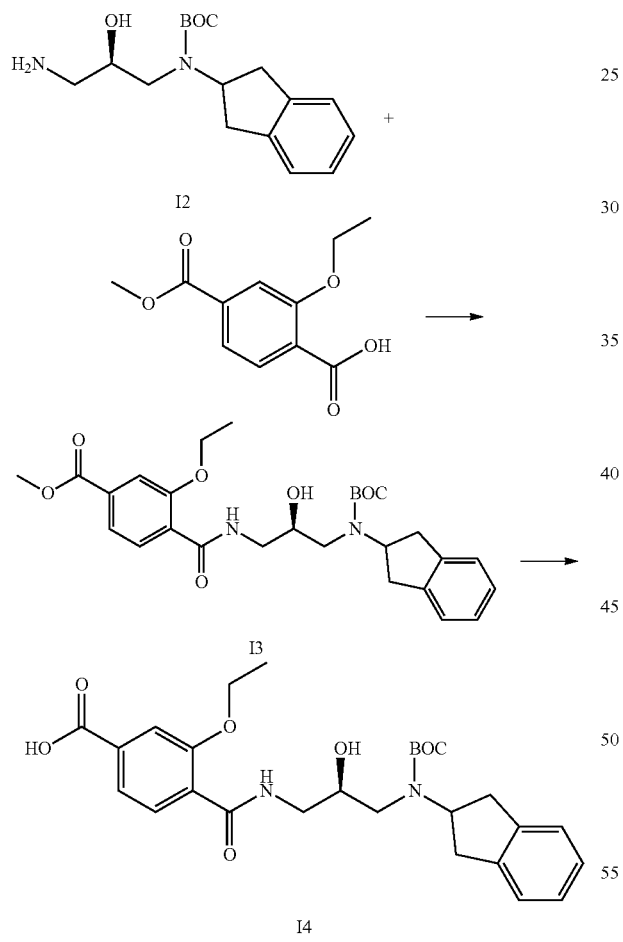

(a) (R)-Methyl 4-((3-((tert-butoxycarbonyl)(2,3-dihydro-1H-inden-2-yl)amino)-2-hydroxypropyl)carbamoyl)-3-ethoxybenzoate (I3)

To a solution of (R)-tert-butyl (3-amino-2-hydroxypropyl)(2,3-dihydro-1H-inden-2-yl) carbamate I2 (300 mg, 0.98 mmol) and 2-ethoxy-4-(methoxycarbonyl)benzoic acid (220 mg, 0.98 mmol) in DCM (10 mL) was added DIPEA (697 µL, 3.92 mmol), EDCl (387 mg, 1.96 mmol) and HOBt (14 mg, 0.10 mmol). The reaction was stirred at room temperature overnight, saturated aqueous NaHCO₃ solution (50 mL) was added, and the aqueous phase was extracted with DCM (3×50 mL), dried (Na₂SO₄), filtered and concentrated. The residue was purified by column chromatography (petroleum ether:EtOAc=3:1) to give the desired product (370 mg, 74%) as a white solid. LCMS RT 3.23 min; m/z 513.3 [M+H]⁺

(b) (R)-4-((3-((tert-butoxycarbonyl)(2,3-dihydro-1H-inden-2-yl)amino)-2-hydroxypropyl)carbamoyl)-3-ethoxybenzoic acid (I4)

To a solution of (R)-methyl 4-((3-((tert-butoxycarbonyl)(2,3-dihydro-1H-inden-2-yl)amino)-2-hydroxypropyl)carbamoyl)-3-ethoxybenzoate I3 (370 mg, 0.72 mmol) in a mixture of THF (10 mL), MeOH (3 mL) and H₂O (1 mL) was added LiOH·H₂O (91 mg, 2.16 mmol). The reaction was stirred at room temperature overnight. The mixture was concentrated under reduced pressure and the residue obtained suspended in water (15 mL). The mixture was acidified to pH 4 with 1 M aqueous HCl and the aqueous phase extracted with DCM (3×30 mL). The pooled organic extracts were dried (Na₂SO₄), filtered and concentrated to give the desired product (370 mg, 100%) as an off-white solid. LCMS RT 3.09 min; m/z 499.3 [M+H]+

(iii) tert-Butyl (S)-3-((R)-2-amino-1-hydroxyethyl)-3,4-dihydroisoquinoline-2(1H)-carboxylate (I9)

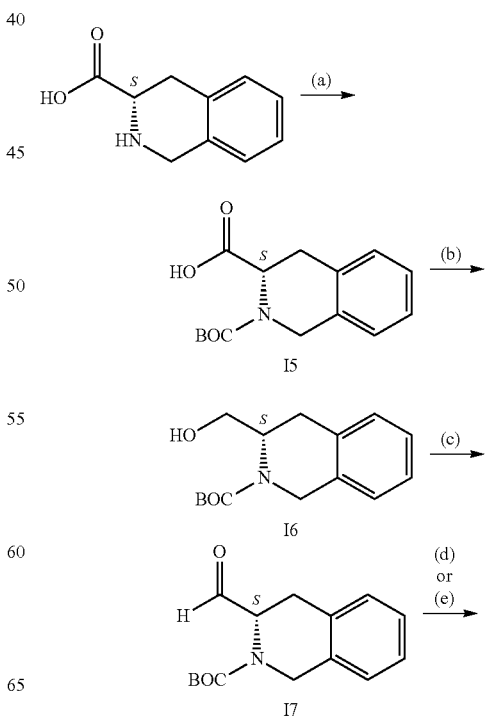

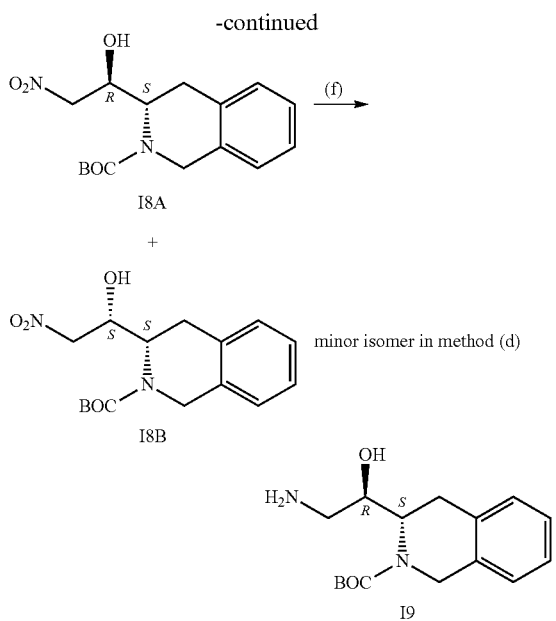

(a) (S)-2-(tert-butoxycarbonyl)-1,2,3,4-tetrahydroisoquinoline-3-carboxylic acid (I5) (S)-1,2,3,4-Tetrahydroisoquinoline-3-carboxylic acid (5.00 g, 28.2 mmol) was vigorously stirred in 1,4-dioxane (100 mL) and water (50 mL). Sodium bicarbonate (4.74 mg, 56.4 mmol) and Boc anhydride (6.77 g, 31.0 mmol) were added and the mixture was stirred vigorously at room temperature. After 17 hours the mixture was concentrated in vacuo and the residue dissolved in water (200 mL). A 30% w/v aqueous solution of sodium hydrogen sulfate monohydrate (30 mL) was added and the mixture extracted with chloroform (3×200 mL). The pooled organic extracts were washed with brine, dried over sodium sulfate and concentrated in vacuo to give the desired compound (7.50 g, 96% yield) as a thick syrup. LCMS-B: RT 3.64 min; m/z 178.1 [M-Boc+2H]$^+$; m/z 276.1 [M-H]$^-$ (b) tert-Butyl (S)-3-(hydroxymethyl)-3,4-dihydroisoquinoline-2(1H)-carboxylate (I6)

(S)-2-(tert-Butoxycarbonyl)-1,2,3,4-tetrahydroisoquinoline-3-carboxylic acid (I5) (7.50 g, 27.0 mmol) was dissolved in THF (150 mL) and CDI (8.77 g, 54.1 mmol) was added. The mixture was stirred for 30 minutes at room temperature then cooled to 0° C. A solution of sodium borohydride (1.16 g, 30.5 mmol) in water (15 mL) was added dropwise. After 40 minutes the mixture was quenched with acetone (25 mL) and concentrated in vacuo. The residue was partitioned between water (250 mL) and ethyl acetate (200 mL). The separated aqueous phase was extracted with ethyl acetate (2×250 mL), the combined organic extracts washed with 5% w/v aqueous NaHSO$_4$ (250 mL), brine (200 mL), dried over sodium sulfate and concentrated in vacuo. The residue was loaded in diethyl ether (50 mL) onto a plug of basic alumina and silica (50 mL each). The plug was eluted with diethyl ether (250 mL) and the eluate evaporated to give the desired compound (5.93 g, 83% yield) as a colourless syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M-Boc+2H]$^+$, 286.2 [M+Na]$^+$ (c) tert-Butyl (S)-3-formyl-3,4-dihydroisoquinoline-2(1H)-carboxylate (I7)

tert-Butyl (S)-3-(hydroxymethyl)-3,4-dihydroisoquinoline-2(1H)-carboxylate (I6) (1.50 g, 5.70 mmol), DCM (25 mL) and DMSO (5 mL) were cooled to 0° C. Triethylamine (2.38 mL, 17.1 mmol) was added, followed by pyridine-sulfur trioxide complex (2.72 g, 17.1 mmol). The mixture was stirred at 0° C. for 10 minutes then allowed to come to room temperature. After 2 hours, saturated sodium bicarbonate (75 mL) and water (75 mL) were added, and the mixture extracted with diethyl ether (3×150 mL). The pooled ether extracts were washed with 1:1 water: saturated aqueous NH$_4$Cl (200 mL), brine (200 mL), dried over sodium sulfate, filtered and concentrated in vacuo to give the desired compound as a colourless oil which was used without further purification.

(d) tert-Butyl (S)-3-((R)-1-hydroxy-2-nitroethyl)-3,4-dihydroisoquinoline-2(1H)-carboxylate (I8A) and tert-butyl (S)-3-((S)-1-hydroxy-2-nitroethyl)-3,4-dihydroisoquinoline-2(1H)-carboxylate (I8B)

A solution of tert-butyl (S)-3-formyl-3,4-dihydroisoquinoline-2(1H)-carboxylate (I7) (5.70 mmol @ 100% conversion) in i-propanol (50 mL) was cooled to 0° C. Nitromethane (1.22 mL, 22.8 mmol) and potassium fluoride (331 mg, 5.70 mmol) were added and the mixture stirred for 18 hours, allowing the temperature to come to room temperature as the ice bath thawed. The mixture was diluted with water (200 mL) and extracted with DCM (3×200 mL). The pooled DCM extracts were washed with brine, dried over sodium sulfate, filtered and concentrated in vacuo. Chromatography (40 g silica cartridge, 0-20% ethyl acetate/hexanes) gave two partly overlapping peaks, which were split into early (8A major, colourless syrup, 697 mg, 37% yield) and late (8B minor, colourless syrup, 170 mg, 9% yield) fractions. Overall: 867 mg, 47% yield.

Data for major isomer tert-butyl (S)-3-((R)-1-hydroxy-2-nitroethyl)-3,4-dihydroisoquinoline-2(1H)-carboxylate I8A:
$^1$H NMR (400 MHz, d$_4$-MeOD) δ 7.25-7.14 (m, 4H), 4.85-4.49 (m, 5H), 4.44 (dd, J=12.6, 9.3 Hz, 1H), 4.37-3.99 (m, overlaps with solvent), 3.19 (dd, J=15.9, 3.2 Hz, 1H), 2.92 (dd, J=15.8, 5.6 Hz, 1H), 1.51 (s, 9H). LCMS-B: RT 3.71 min; m/z 223.2 [M-Boc+2H]$^+$, 345.2 [M+Na]$^+$; m/z 321.2 [M-H]$^-$ Data for minor isomer tert-butyl (S)-3-((S)-1-hydroxy-2-nitroethyl)-3,4-dihydroisoquinoline-2(1H)-carboxylate I8B:
$^1$H NMR (400 MHz, d$_4$-MeOD) δ 7.25-7.11 (m, 4H), 4.75 (d, J=16.5 Hz, 1H), 4.68-4.48 (m, 4H), 4.42-4.23 (m, overlaps with residual nitromethane), 3.06 (dd, J=16.3, 6.1 Hz, 1H), 2.91 (d, J=16.1 Hz, 1H), 1.50 (s, 9H). LCMS-B: RT 3.70 min; m/z 223.2 [M-Boc+2H]$^+$, 345.2 [M+Na]$^+$; m/z 321.2 [M-H]$^-$ (e) tert-Butyl (S)-3-((R)-1-hydroxy-2-nitroethyl)-3,4-dihydroisoquinoline-2(1H)-carboxylate (I8A)

Copper catalyst used:

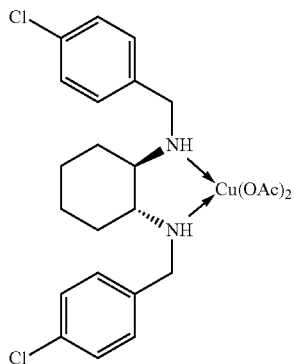

tert-Butyl (S)-3-formyl-3,4-dihydroisoquinoline-2(1H)-carboxylate (I7) (1.9 mmol @100% conversion), absolute ethanol (5 mL), nitromethane (1.02 mL, 19.0 mmol) and the copper catalyst (91 mg, 10 mol %) (see above FIGURE, prepared according to Tetrahedron:

Asymmetry (2008) 2310-2315) were stirred at room temperature. After 90 hours the mixture was concentrated in vacuo, chromatography (40 g silica cartridge, 0-15% ethyl acetate/hexanes) gave the desired compound (352 mg, 58% yield over two steps). $^1$H NMR (400 MHz, $d_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M−H]$^−$ (f) tert-Butyl (S)-3-((R)-2-amino-1-hydroxyethyl)-3,4-dihydroisoquinoline-2(1H)-carboxylate (I9)

tert-Butyl (S)-3-((R)-1-hydroxy-2-nitroethyl)-3,4-dihydroisoquinoline-2(1H)-carboxylate (I8A) (1.54 g, 4.78 mmol), absolute ethanol (75 mL) and 10% Pd/C (53% wetted with water, 1.5 g) were stirred under hydrogen (balloon). After 3 hours the mixture was filtered through celite, the celite was washed with absolute ethanol (100 mL) and the combined filtrates concentrated in vacuo to give the desired compound (1.34 g, 96% yield) as a pale grey-green syrup. LCMS-B: RT 3.27 min, m/z 293.2 [M+H]$^+$
Alternate Synthesis Method (a) (S)-2-(tert-Butoxycarbonyl)-1,2,3,4-tetrahydroisoquinoline-3-carboxylic acid (I5)

(S)-1,2,3,4-Tetrahydroisoquinoline-3-carboxylic acid (50.0 g, 282 mmol) was vigorously stirred in a mixture of 1,4-dioxane (1000 mL) and water (500 mL). Sodium bicarbonate (47.4 g, 564 mmol) and Boc anhydride (67.7 g, 310 mmol) were added and the reaction was stirred vigorously at room temperature for 6 days. The mixture was concentrated in vacuo and the residue dissolved in water (2000 mL). A 30% w/v aqueous solution of sodium hydrogen sulfate monohydrate (300 mL) was added and the mixture extracted with chloroform (3×1000 mL). The pooled organic extracts were washed with brine, dried over sodium sulfate and concentrated in vacuo to give the desired compound (90.0 g, quantitative) as a thick syrup. LCMS-B: RT 3.64 min; m/z 178.1 [M-Boc+2H]$^+$; m/z 276.1 [M−H]$^−$ (b) tert-Butyl (S)-3-(hydroxymethyl)-3,4-dihydroisoquinoline-2(1H)-carboxylate (I6)

(S)-2-(tert-Butoxycarbonyl)-1,2,3,4-tetrahydroisoquinoline-3-carboxylic acid (I5) (54.0 g, 195 mmol) was dissolved in THF (1000 mL) and CDI (63.2 g, 390 mmol) was added. The mixture was stirred for 2 hours at 30° C. then cooled to 0° C. A solution of sodium borohydride (14.7 g, 390 mmol) in water (120 mL) was added dropwise. After 3 hours the mixture was quenched with acetone (300 mL) and concentrated in vacuo. The residue was partitioned between water (1000 mL) and ethyl acetate (1000 mL). The separated aqueous phase was extracted with ethyl acetate (4×500 mL) and the combined organic extracts washed with 5% w/v aqueous NaHSO$_4$ (1000 mL), brine (500 mL), dried over sodium sulfate and concentrated in vacuo. The residue was purified by chromatography (5-20% ethyl acetate/petroleum ether) to give the desired compound (30.4 g, 59% yield) as a yellow syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M-Boc+2H]$^+$, 286.2 [M+Na]$^+$ (c) tert-Butyl (S)-3-formyl-3,4-dihydroisoquinoline-2(1H)-carboxylate (I7)

tert-Butyl (S)-3-(hydroxymethyl)-3,4-dihydroisoquinoline-2(1H)-carboxylate (I6) (16 g, 0.06 mol), DCM (250 mL) and DMSO (75 mL) were cooled to 0° C. Triethylamine (25.1 mL, 0.18 mol) was added, followed by pyridine-sulfur trioxide complex (28.6 g, 0.18 mol). The mixture was stirred at 0° C. for 30 minutes then allowed to come to room temperature and stirred at room temperature overnight. Saturated sodium bicarbonate (200 mL) and water (200 mL) were added, and the mixture extracted with diethyl ether (3×300 mL). The pooled ether extracts were washed with 1:1 water: saturated aqueous NH$_4$Cl (200 mL), dried over sodium sulfate and concentrated in vacuo to give the desired compound (16.0 g) as an orange oil which was used without further purification.

(e) tert-Butyl (S)-3-((R)-1-hydroxy-2-nitroethyl)-3,4-dihydroisoquinoline-2(1H)-carboxylate (I8A)

To a solution of tert-butyl (S)-3-formyl-3,4-dihydroisoquinoline-2(1H)-carboxylate (I7) (0.06 mol @100% conversion) in absolute ethanol (50 mL) was added a solution of the copper catalyst (6.8 g, 20 mol %) (see above FIGURE, prepared according to Tetrahedron: Asymmetry (2008) 2310-2315) in absolute ethanol (10 mL). The mixture was cooled to 0° C. and nitromethane (36.0 g, 0.6 mol) was added. The reaction was stirred at 0° C. for 3 days, the mixture was concentrated in vacuo and purified by chromatography (5% ethyl acetate/petroleum ether) to give the desired compound (7.5 g, 39% yield over two steps). $^1$H NMR (400 MHz, $d_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M−H]$^−$

(f) tert-Butyl (S)-3-((R)-2-amino-1-hydroxyethyl)-3,4-dihydroisoquinoline-2(1H)-carboxylate (I9)

To a solution of tert-butyl (S)-3-((R)-1-hydroxy-2-nitroethyl)-3,4-dihydroisoquinoline-2(1H)-carboxylate (I8A) (7.5 g, 23.3 mmol) in absolute ethanol (100 mL) was added 10% Pd/C (7.5 g) and the reaction was stirred under an atmosphere of hydrogen. After 3 hours, the mixture was filtered through Celite, the Celite was washed with absolute ethanol (200 mL) and the combined filtrates concentrated in vacuo to give the desired compound (5.3 g, 78% yield) as a pale grey solid. LCMS-B: RT 3.27 min, m/z 293.2 [M+H]$^+$

(iv) 4-(((R)-2-((S)-2-(tert-butoxycarbonyl)-1,2,3,4-tetrahydroisoquinolin-3-yl)-2-hydroxyethyl)carbamoyl)-3-ethoxybenzoic acid (I16)

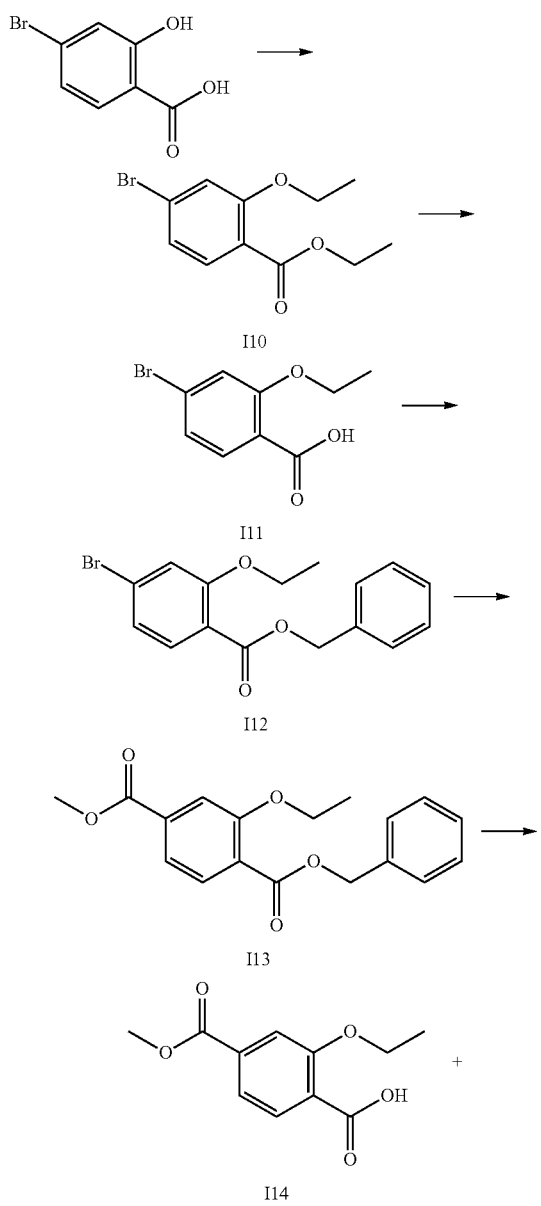

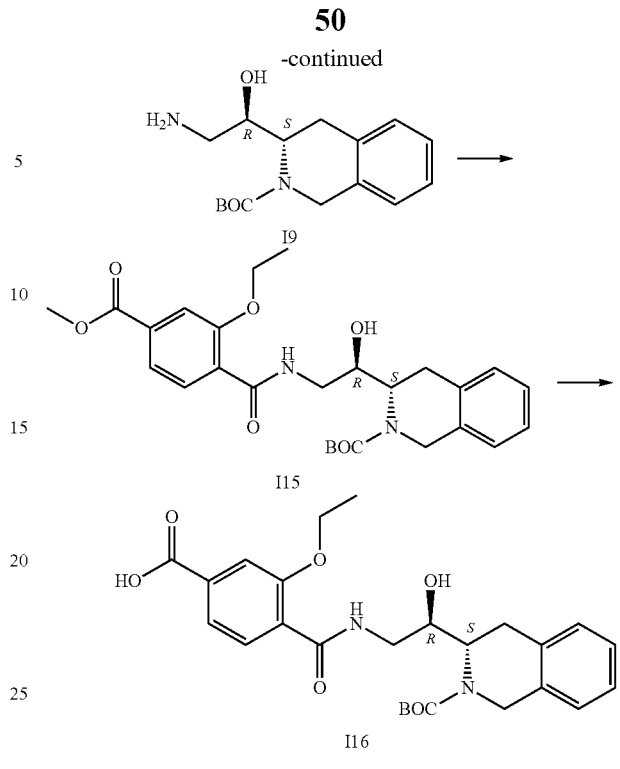

(a) Ethyl-4-bromo-2-ethoxybenzoate (I10)

To a mixture of 4-bromo-2-hydroxybenzoic acid (20.0 g, 92.6 mmol) and $K_2CO_3$ (38.4 g, 278 mmol) in dimethylsulfoxide (50 mL) at 40° C. was added ethyl bromide (15.2 g, 139 mmol) dropwise over 30 minutes, the reaction mixture was stirred for 2 hours then further ethyl bromide (15.2 g, 139 mmol) was added over 30 minutes. The reaction was stirred a further 8 hours then diluted with $CH_2Cl_2$ (150 mL) and filtered. The filtrate was washed with water (200 mL×10), brine (200 mL×3), dried ($Na_2SO_4$), filtered and concentrated to give the title compound as a brown solid (24.3 g, 96%): LCMS: RT 2.93 min; m/z 273.0 [M+H]$^+$.

(b) 4-Bromo-2-ethoxybenzoic acid (I11)

To a solution of ethyl 4-bromo-2-ethoxybenzoate I10 (24.1 g, 88.6 mmol) in a mixture of THF (150 mL), methanol (15 mL) and water (15 mL) was added LiOH $H_2O$ (18.6 g, 44.3 mmol). The resulting mixture was stirred at room temperature for 24 hours. The solvent was removed, and the residue diluted with water (200 mL). The pH of the aqueous mixture was adjusted to 6 by addition of 2 M aqueous HCl. The aqueous mixture was extracted with $CH_2Cl_2$ (150 mL×3) and the combined organic layers washed with brine (100 mL×3), dried ($Na_2SO_4$), filtered and concentrated to give the title compound as a yellow solid (19.8 g, 92%): LCMS: RT 2.47 min; m/z, 244.9/246.9 [M+H]$^+$.

(c) Benzyl-4-bromo-2-ethoxybenzoate (I12)

To a solution of 4-bromo-2-ethoxybenzoic acid I11 (16.4 g, 67.2 mmol) in acetonitrile (75 mL) was added benzyl bromide (13.8 g, 80.7 mmol) and $K_2CO_3$ (18.6 g, 134.4 mmol). The resulting mixture was stirred at 40° C. overnight. The reaction mixture was filtered and concentrated. The residue was diluted with $CH_2Cl_2$ (50 mL) and washed with water (100 mL×2), brine (70 mL×3), dried (Na$_2$SO$_4$), filtered and concentrated. The crude product was purified by column chromatography (1% EtOAc in petroleum ether) to give the title compound as a light-yellow oil (20.9 g, 93%): LCMS: RT 3.31 min; m/z 334.9 [M+H]$^+$.

(d) 1-Benzyl 4-methyl 2-ethoxyterephthalate (I13)

To a solution of benzyl 4-bromo-2-ethoxybenzoate I12 (20.0 g, 59.9 mmol) in methanol (100 mL) was added Pd(dppf)Cl$_2$ (2.2 g, 3 mmol) and triethylamine (13.3 g, 131.7 mmol). The resulting mixture was heated at reflux overnight under an atmosphere of carbon monoxide. The reaction mixture was concentrated and the residue obtained was diluted with water and was extracted with CH$_2$Cl$_2$ (50 mL×3). The combined organic layers were washed with brine (60 mL×2), dried (Na$_2$SO$_4$), filtered and concentrated. The residue was purified by column chromatography (2% EtOAc in petroleum ether) to give the title compound as a white solid (15.1 g, 81%): LCMS: RT 3.03 min; m/z 315.1 [M+H]$^+$.

(e) 2-Ethoxy-4-(methoxycarbonyl)benzoic acid (I14)

To a solution of 1-benzyl 4-methyl 2-ethoxyterephthalate I13 (14.9 g, 47.4 mmol) in THF (100 mL) was added 10% Pd/C (1.5 g). The resulting mixture was stirred at room temperature overnight under H2. The catalyst was removed by filtration through Celite and the filter cake washed with THF (50 mL). The filtrate was concentrated and the residue was diluted with water. The pH of the aqueous solution was adjusted to 6 by addition of 2 M aqueous HCl and the resultant mixture extracted with CH$_2$Cl$_2$ (50 mL×3). The combined organic layers were washed with brine (50 mL×2), dried (Na$_2$SO$_4$), filtered and concentrated to give the title compound as a white solid (10.2 g, 96%): LCMS: RT 2.13 min; m/z 225.0 [M+H]$^+$.

(f) (S)-tert-Butyl-3-((R)-2-(2-ethoxy-4-(methoxycarbonyl)benzamido)-1-hydroxyethyl)-3,4-dihydroisoquinoline-2(1H)-carboxylate (I15)

To a solution of 2-ethoxy-4-(methoxycarbonyl)benzoic acid I14 (1.7 g, 7.5 mmol) in CH$_2$Cl$_2$ (50 mL) were added (S)-tert-butyl 3-((R)-2-amino-1-hydroxyethyl)-3,4-dihydroisoquinoline-2(1H)-carboxylate I9 (2.0 g, 6.8 mmol), HOBt (100 mg, 0.7 mmol), DIPEA (3.9 g, 20.4 mmol) and EDCI (2.6 g, 13.6 mmol). The resulting mixture was stirred at room temperature overnight. The mixture was diluted with water (80 mL) and extracted with CH$_2$Cl$_2$ (80 mL×3). The combined organic layers were washed with water (150 mL), brine (150 mL), dried (Na$_2$SO$_4$), filtered and concentrated. The residue was purified by column chromatography (33% EtOAc in petroleum ether) to give the title compound as a yellow solid (2.2 g, 65%):
LCMS: RT 3.12 min; m/z 499.2 [M+H]$^+$.

(g) 4-(((R)-2-((S)-2-(tert-Butoxycarbonyl)-1,2,3,4-tetrahydroisoquinolin-3-yl)-2-hydroxyethylcarbamoyl)-3-ethoxybenzoic acid (I16)

To a solution of (S)-tert-butyl-3-((R)-2-(2-ethoxy-4-(methoxycarbonyhbenzamido)-1-hydroxyethyl)-3,4-dihydroisoquinoline-2(1H)-carboxylate 15 (2.1 g, 4.2 mmol) in methanol (4 mL) was added a solution of NaOH (340 mg, 8.4 mmol) in water (6 mL). The resulting mixture was stirred at room temperature overnight. The solvent was removed, and the residue diluted with water (30 mL). The pH of the aqueous mixture was adjusted to 5 by addition of 2 M aqueous HCl solution. The aqueous layer was then extracted with CH$_2$Cl$_2$ (50 mL×4) and the combined organic layers washed with brine, dried (Na$_2$SO$_4$) and concentrated to give the title compound as a yellow solid (1.9 g, 95%): LCMS: RT 2.95 min; m/z 485.2 [M+H]$^+$.

(v) 4-(3-Oxa-8-azabicyclo[3.2.1]octane-8-carbonyl)-2-ethoxybenzoic acid I20

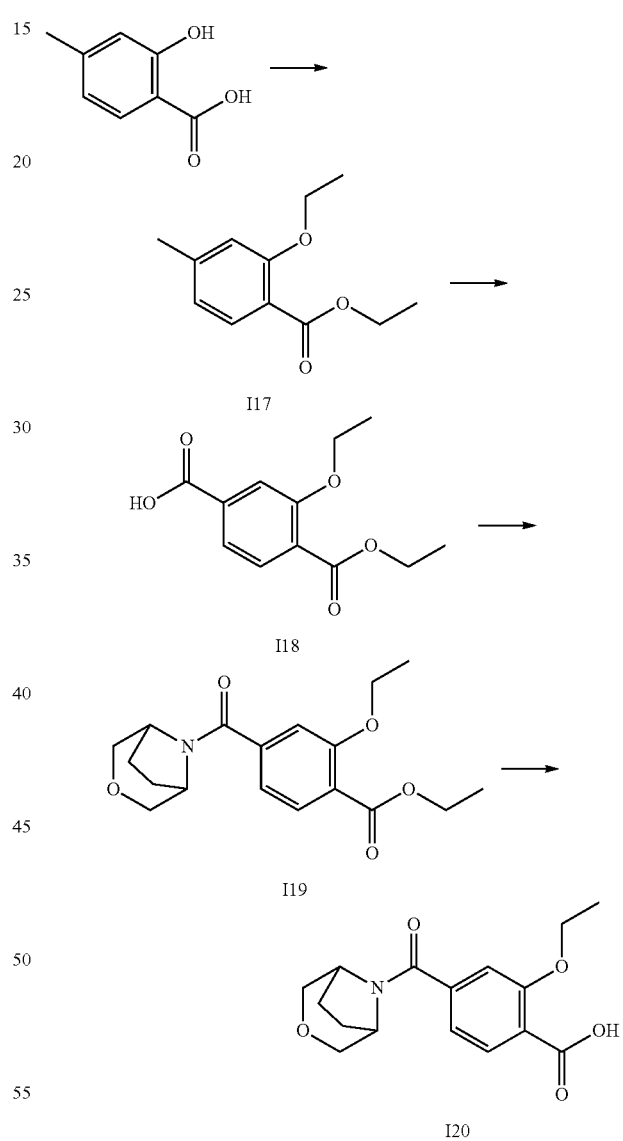

(a) Ethyl-2-ethoxy-4-methylbenzoate I17

To a mixture of 2-hydroxy-4-methylbenzoic acid (8.2 g, 53.9 mmol) and K$_2$CO$_3$ (22.4 g, 161.7 mmol) in dimethylsulfoxide (70 mL) at 40° C. was added ethyl iodide (12.6 g, 80.8 mmol) dropwise over a period of 30 min. The reaction was stirred for 2 hours then further ethyl iodide (12.6 g, 80.8 mmol) was added over 30 min. The reaction mixture was stirred a further 8 hours at 40° C., diluted with CH$_2$Cl$_2$ (150 mL) and filtered. The filtrate was washed with water (200 mL×10) and brine (200 mL×2), dried (Na$_2$SO$_4$), filtered and concentrated to give the desired compound as a yellow liquid (10.1 g, 90%): LCMS: RT 2.70 min; m/z 209.1 [M+H]$^+$.

(b) 3-Ethoxy-4-(ethoxycarbonyl)-benzoic acid I18

To a solution of ethyl 2-ethoxy-4-methylbenzoate I17 (10.0 g, 48.1 mmol) in a mixture of pyridine (25 mL) and water (75 mL) was added KMnO$_4$ (22.8 g, 144.2 mmol). The resulting mixture was heated at 50° C. for 48 hours, then cooled and allowed to stir at room temperature for 24 hours. The mixture was filtered and the filter cake washed with hot water. The combined aqueous filtrates were washed with EtOAc (75 mL×3) and acidified with 2M aqueous HCl solution. The mixture was extracted with CH$_2$Cl$_2$ (150 mL×3). The combined organic layers were washed with brine, dried (Na$_2$SO$_4$), filtered and concentrated to give the desired compound as a white solid (5.0 g, 44%): LCMS: RT 0.25 min; m/z 239.0 [M+H]$^+$.

(c) Ethyl 4-(3-oxa-8-azabicyclo[3.2.1]octane-8-carbonyl)-2-ethoxybenzoate I19

To a solution of 3-ethoxy-4-(ethoxycarbonyl)benzoic acid I18 (2.5 g, 10.4 mmol) in CH$_2$Cl$_2$ (20 mL) was added 3-oxa-8-azabicyclo[3.2.1]octane hydrochloride (1.42 g, 9.5 mmol), HOBt (135.1 mg, 1.0 mmol), DIPEA (2.5 g, 19.0 mmol) and EDCl (2.2 g, 11.4 mmol). The resulting mixture was stirred at room temperature overnight. The mixture was partitioned with saturated aqueous NaHCO$_3$, and extracted with CH$_2$Cl$_2$ (20 mL×2). The combined organic layers were washed with brine, dried (Na$_2$SO$_4$), filtered and concentrated. The residue was purified by column chromatography (1% methanol in dichloromethane) to give the desired compound as a yellow oil (2.5 g, 80%): LCMS: RT 2.40 min; m/z 334.1 [M+H]$^+$.

(d) 4-(3-Oxa-8-azabicyclo[3.2.1]octane-8-carbonyl)-2-ethoxybenzoic acid I20

To a solution of ethyl-4-(3-oxa-8-azabicyclo-[3.2.1]-octane-8-carbonyl)-2-ethoxybenzoate I19 (2.4 g, 7.2 mmol) in a mixture of THF (20 mL), methanol (2 mL) and water (2 mL) was added LiOH H$_2$O (1.5 g, 36 mmol). The resulting mixture was stirred at room temperature for 24 h. The solvent was removed, and the residue obtained diluted with water (20 mL). The pH of the aqueous mixture was adjusted to 6 by addition of a 2 M aqueous HCl solution. The mixture was extracted with CH$_2$Cl$_2$ (20 mL×3) and the combined organic layers washed with brine (10 mL×2), dried (Na$_2$SO$_4$), filtered and concentrated to give the desired compound as a yellow oil (1.7 g, 79%): $^1$H NMR (400 MHz, d$_4$-MeOD) δ 7.83 (d, J=7.8 Hz, 1H), 7.19 (d, J=1.0 Hz, 1H), 7.10 (dd, J=7.8, 1.3 Hz, 1H), 4.65 (br s, 1H), 4.20 (q, J=7.0 Hz, 2H), 3.97 (br s, 1H), 3.82 (d, J=10.8 Hz, 1H), 3.72 (d, J=11.0 Hz, 2H), 3.59 (d, J=10.9 Hz, 1H), 2.13-1.94 (m, 4H), 1.45 (t, J=7.0 Hz, 3H). LCMS: RT 1.20 min; m/z 306.1 [M+H]$^+$.

EXAMPLES

Example 1: 2-Ethoxy-N—((R)-2-hydroxy-2-((S)-1,2,3,4-tetrahydroisoquinolin-3-yl)ethyl)-4-hydroxy-3-oxa-9-azabicyclo[3.3.1]nonane-9-carbonyl)benzamide hydrochloride (1)

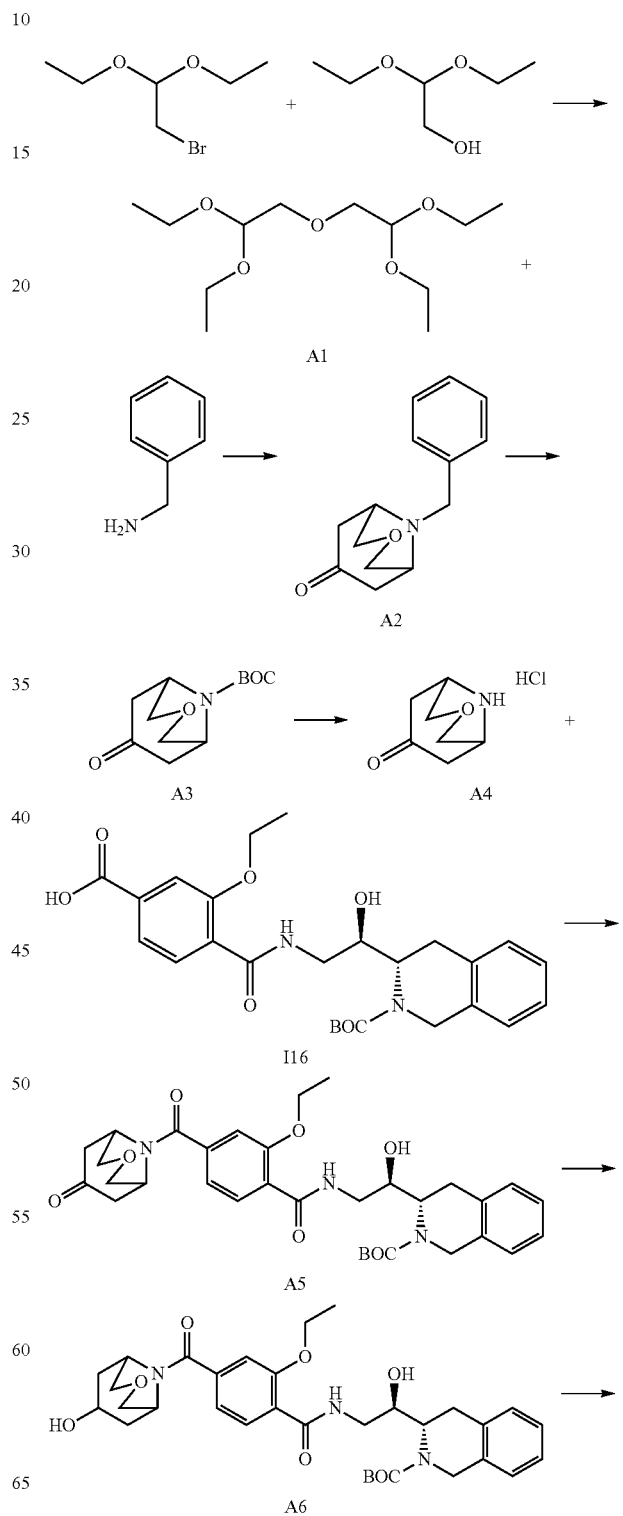

-continued

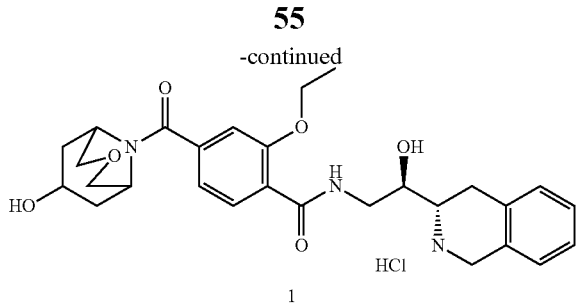

(a) 2-(2,2-Diethoxyethoxy)-1,1-diethoxyethane (A1)

To a suspension of NaH (60% dispersion in mineral oil, 3.8 g, 95.0 mmol) in xylene (100 mL) was added 2,2-diethoxyethanol (11.6 g, 86.4 mmol) under $N_2$. The mixture heated at 110° C. for 2 hours, then cooled to room temperature and 2-bromo-1,1-diethoxyethane (25.6 g, 130.0 mmol) added. The reaction was heated at 110° C. overnight, then cooled to room temperature and the organic layer washed with water, dried ($Na_2SO_4$), filtered and concentrated. The residue obtained was purified by distillation to give the title compound (7 g, 33%) as colorless oil.

(b) 9-Benzyl-3-oxa-9-azabicyclo[3.3.1]nonan-7-one (A2)

2-(2,2-Diethoxyethoxy)-1,1-diethoxyethane A1 (5 g, 20.0 mmol) in a mixture of acetic acid (1.2 mL) and water (5 mL) was heated at reflux for 1 hour then cooled to room temperature. Benzylamine hydrochloride (2.1 g, 20.0 mmoL) and 3-oxopentanedioic acid (2.5 g, 16.6 mmoL), NaOAc (0.69 g, 83.8 mmoL) and water (10 mL) were added and the reaction heated at 50° C. for 5 hours. The reaction was cooled to room temperature and aqueous NaOH solution (42 mL, 50% w/v) was added into the mixture. The aqueous phase was extracted with EtOAc (3×30 mL) and the combined organic fractions concentrated and purified by column chromatography (100% petroleum ether to 10% EtOAc in petroleum ether) to give the title compound as a yellow solid. LCMS: RT 0.50 min, m/z 232.1 $[M+H]^+$

(c) tert-Butyl 7-oxo-3-oxa-9-azabicyclo[3.3.1]nonane-9-carboxylate (A3)

A mixture of 9-benzyl-3-oxa-9-azabicyclo[3.3.1]nonan-7-one A2 (425 mg, 2.2 mmol), $(Boc)_2O$ (1.3 g, 6.5 mmol) and 10% Pd/C (50 mg) in MeOH (10 mL) was stirred vigorously under an atmosphere of H2 gas overnight. The catalyst was removed by filtration through celite and the filtrate was concentrated. The residue obtained was purified by column chromatography (100% petroleum ether to 10% EtOAc in petroleum ether) to give the title compound as a yellow solid (250 mg, 57%). LCMS: RT 0.53 min, m/z 264.1 $[M+Na]^+$.

(d) 3-Oxa-9-azabicyclo[3.3.1]nonan-7-one hydrochloride (A4)

A solution of tert-butyl 7-oxo-3-oxa-9-azabicyclo[3.3.1]nonane-9-carboxylate A3 (160 mg, 0.66 mmol) in HCl in $Et_2O$ (3 M solution, 3 mL) was stirred at room temperature for 2-3 hours. The mixture was concentrated and the crude product obtained washed with ether to give the desired product as a yellow solid (120 mg, 100%). LCMS: RT 0.24 min, m/z 142.1 $[M+H]^+$.

(e) (S)-tert-Butyl-3-((R)-2-(2-ethoxy-4-(7-oxo-3-oxa-9-azabicyclo[3.3.1]nonane-9-carbonyl)benzamido)-1-hydroxyethyl)-3,4-dihydroisoquinoline-2(1H)-carboxylate (A5)

To a solution of -oxa-9-azabicyclo[3.3.1]nonan-7-one hydrochloride A4 (80 mg, 0.37 mmol) and 4-(((R)-2-((S)-2-(tert-butoxycarbonyl)-1,2,3,4-tetrahydroisoquinolin-3-yl)-2-hydroxyethyl) carbamoyl)-3-ethoxybenzoic acid I16 (151 mg, 0.31 mmol) in DCM (10 mL) was added EDCl (107 mg, 0.56 mmol), HOBt (76 mg, 0.56 mmol) and DIPEA (145 mg, 1.12 mmol). The reaction was stirred at room temperature for 3 hours, then concentrated. The residue obtained was purified by column chromatography (100% DCM to 10% MeOH in DCM) to give the title compound as a yellow solid (150 mg, 79%). LCMS: RT 2.74 min, m/z 608.3 $[M+H]^+$.

(f) (3S)-tert-Butyl 3-((1R)-2-(2-ethoxy-4-(7-hydroxy-3-oxa-9-azabicyclo[3.3.1]nonane-9-carbonyl)benzamido)-1-hydroxyethyl)-3,4-dihydroisoquinoline-2(1H)-carboxylate (A6)

A mixture of (S)-tert-butyl 3-((R)-2-(2-ethoxy-4-(7-oxo-3-oxa-9-azabicyclo[3.3.1]nonane-9-carbonyl)benzamido)-1-hydroxyethyl)-3,4-dihydroisoquinoline-2(1H)-carboxylate A5 (110 mg, 0.18 mmol) in THF (5 mL) was added $NaBH_4$ (34 mg, 0.90 mmol) and the reaction stirred at room temperature for 3 hours. The mixture was concentrated and the residue obtained purified by column chromatography (100% DCM to 10% MeOH in DCM) to give the title compound as a white solid (70 mg, 63%). LCMS: RT 2.78 min, m/z 632.3 $[M+Na]^+$. The relative stereochemistry of the bicyclic alcohol was not determined.

(g) 2-Ethoxy-N—((R)-2-hydroxy-2-((S)-1,2,3,4-tetrahydroisoquinolin-3-yl)ethyl)-4-(7-hydroxy-3-oxa-9-azabicyclo[3.3.1]nonane-9-carbonyl)benzamide hydrochloride (1)

A solution of (3S)-tert-butyl 3-((1R)-2-(2-ethoxy-4-(−7-hydroxy-3-oxa-9-azabicyclo[3.3.1] nonane-9-carbonyl)benzamido)-1-hydroxyethyl)-3,4-dihydroisoquinoline-2(1H)-carboxylate A6 (50 mg, 0.082 mmol) in a solution of HCl in $Et_2O$ (3M, 5 mL) was stirred at room temperature for 2-3 h. The mixture was concentrated and the crude product washed with diethyl ether to give the desired product as a white solid (30 mg, 90%). $^1$H NMR (400 MHz, $CDCl_3$) δ 7.97 (d, J=8.0 Hz, 1H), 7.31-7.22 (m, 4H), 7.19 (d, J=0.8 Hz, 1H), 7.11 (dd, J=7.6 Hz, 1.2 Hz, 1H), 4.68 (br s, 1H), 4.43 (q, J=7.2 Hz, 2H), 4.27-4.22 (m, 3H), 4.0-4.97 (m, 2H), 3.89-3.85 (m, 3H), 3.76-3.70 (m, 2H), 3.66-3.59 (m, 2H), 3.27 (br s, 1H), 3.22-3.17 (m, 1H), 2.39-2.33 (m, 1H), 2.23-2.18 (m, 1H), 1.96 (m, 1H), 1.82-1.78 (m, 1H), 1.43 (t, J=7.2 Hz, 3H); LCMS: RT 3.25 min, m/z 510.3 $[M+H]^+$.

Example 2: N—((S)-3-((2,3-Dihydro-1H-inden-2-yl)amino)-2-hydroxypropyl)-2-ethoxy-4-(-7-hydroxy-3-oxa-9-azabicyclo[3.3.1]nonane-9-carbonyl)benzamide (2)

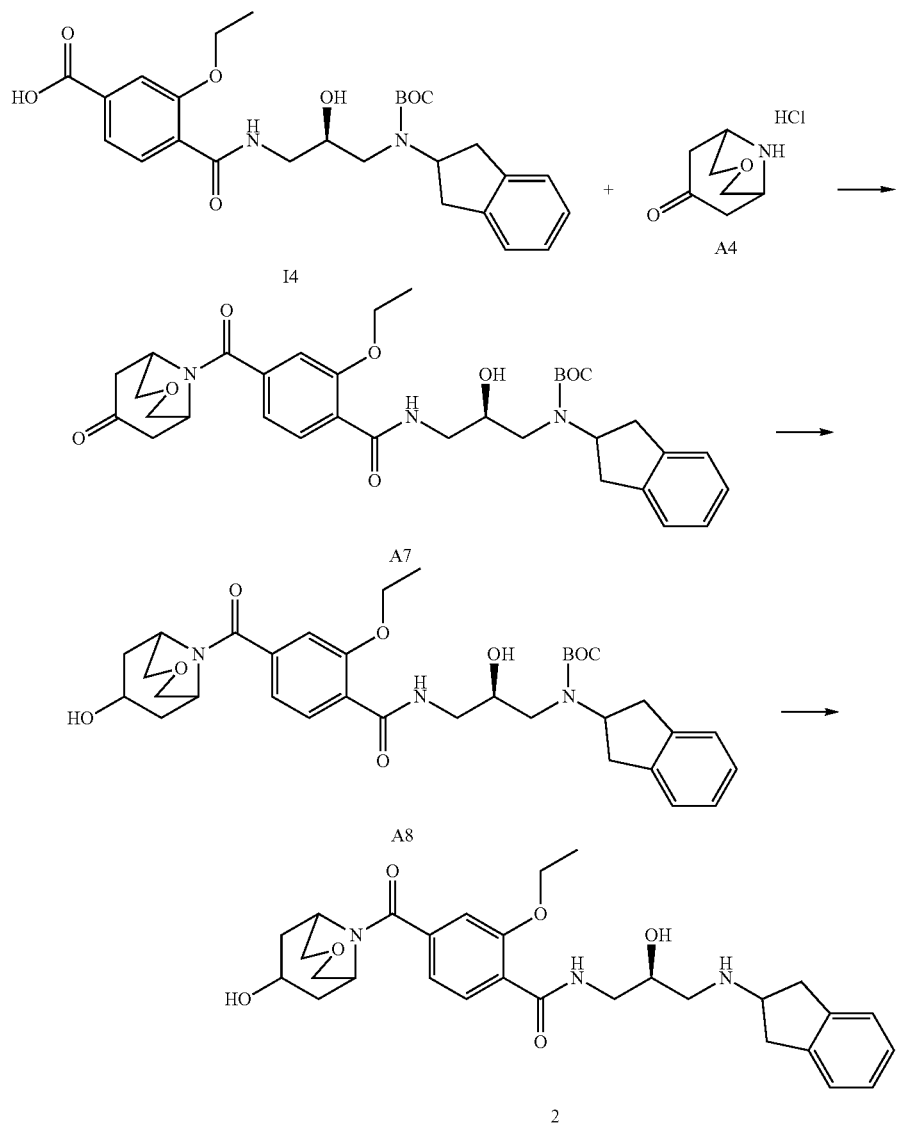

(a) tert-Butyl (2,3-dihydro-1H-inden-2-yl)((R)-3-(2-ethoxy-4-7-oxo-3-oxa-9-azabicyclo[3.3.1]nonane-9-carbonyl)benzamido)-2-hydroxypropyl)carbamate (A7)

To a solution of (R)-4-((3-((tert-butoxycarbonyl)(2,3-dihydro-1H-inden-2-yl)amino)-2-hydroxypropyl)carbamoyl)-3-ethoxybenzoic acid I4 (200 mg, 0.40 mmol) and 3-oxa-9-azabicyclo[3.3.1]nonan-7-one hydrochloride A4 (76 mg, 0.44 mmol) in DCM (5 mL) was added DIPEA (0.356 mL, 2.00 mmol), EDCl (153 mg, 0.81 mmol) and HOBt (5 mg, 0.07 mmol). The resultant mixture was stirred at room temperature overnight. Saturated aqueous NaHCO$_3$ (30 mL) was added, and the mixture extracted with DCM (3×30 mL). The combined organic layers were dried (Na$_2$SO$_4$), filtered and concentrated. The residue obtained was purified by preparative TLC (DCM:MeOH=10:1) to give the desired product (60 mg, 24%) as a grey solid. LCMS RT 2.85 min; m/z 622.3 [M+H]$^+$ (b) tert-Butyl (2,3-dihydro-1H-inden-2-yl)((R)-3-(2-ethoxy-4-(-7-hydroxy-3-oxa-9-azabicyclo[3.3.1]nonane-9-carbonyl)benzamido)-2-hydroxypropyl)carbamate (A8)

To a solution of tert-butyl (2,3-dihydro-1H-inden-2-yl)((R)-3-(2-ethoxy-4-(7-oxo-3-oxa-9-azabicyclo[3.3.1]nonane-9-carbonyl)benzamido)-2-hydroxypropyl)carbamate A7 (60 mg, 0.10 mmol) in MeOH (5 mL) was added NaBH$_4$(11 mg, 0.30 mmol) and the reaction stirred at room temperature for 3 hours. The solvent was removed and the residue purified by preparative TLC (DCM:MeOH=10:1) to give the title compound (50 mg, 81%) as a white solid. LCMS: RT 1.31 min; m/z 524.3 [M-Boc+2H]⁺.

(c) N—((S)-3-((2,3-Dihydro-1H-inden-2-yl)amino)-2-hydroxypropyl)-2-ethoxy-4-(7-hydroxy-3-oxa-9-azabicyclo[3.3.1]nonane-9-carbonyl)benzamide (2)

tert-Butyl (2,3-dihydro-1H-inden-2-yl)((R)-3-(2-ethoxy-4-(-7-hydroxy-3-oxa-9-azabicyclo[3.3.1]nonane-9-carbonyl)benzamido)-2-hydroxypropyl)carbamate A8 (50 mg, 0.08 mmol) was stirred in a solution of 2.0 M solution of HCl in Et$_2$O at room temperature for 2-3 hours. Saturated aqueous NaHCO$_3$ (30 mL) was added, and the mixture was extracted with DCM (3×30 mL). The combined organic layers were dried (Na$_2$SO$_4$), filtered and concentrated. The reaction was repeated on another 60 mg of starting material and the combined crude products were purified by preparative TLC (DCM:MeOH=10:1) provide the desired product (30 mg, 30%) as a white solid. $^1$H NMR (400 MHz, MeOD) δ 8.01 (d, J=8.0 Hz, 1H), 7.24-7.11 (m, 6H), 4.66 (m, 2H), 4.29 (q, J=6.8 Hz, 2H), 4.06-3.76 (m, 7H), 3.63-3.59 (m, 1H), 3.54-3.49 (m, 1H), 3.37-3.33 (m, 2H), 3.09-2.90 (m, 4H), 2.40-2.34 (m, 1H), 2.25-2.18 (m, 1H), 2.04-1.95 (m, 1H), 1.83-1.79 (m, 1H), 1.53 (t, J=6.8 Hz, 3H); LCMS: RT 1.26 min; m/z 524.3 [M+H]⁺.

Example 3: 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)-N-methylbenzamide hydrochloride (3)

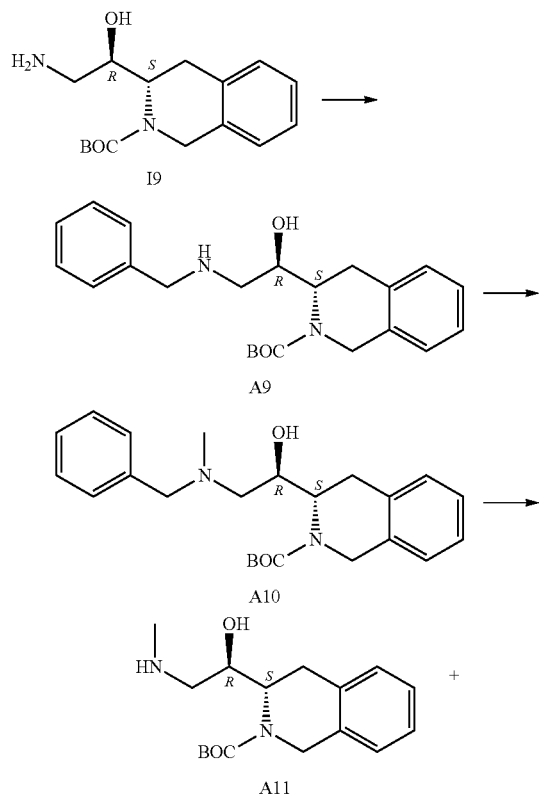

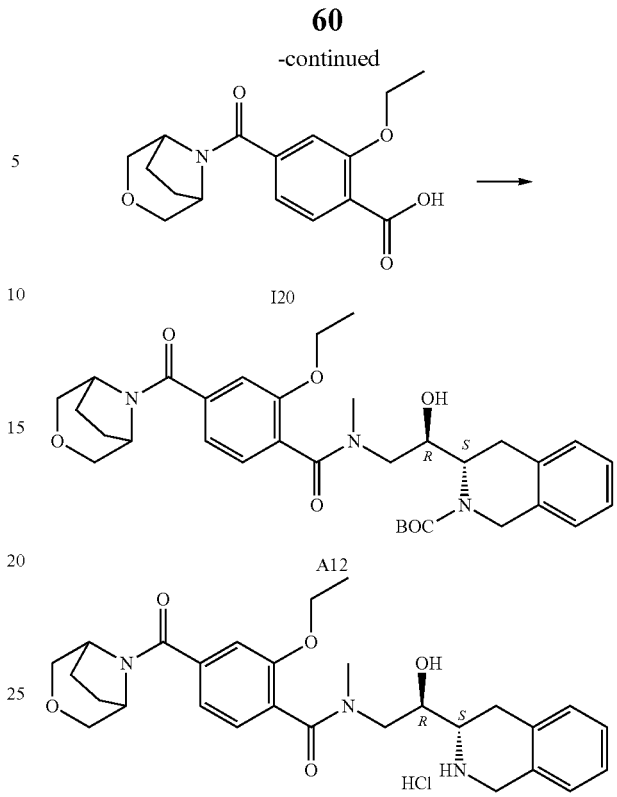

(a) (S)-tert-Butyl 3-((R)-2-(benzylamino)-1-hydroxyethyl)-3,4-dihydroisoquinoline-2(1H)-carboxylate (A9)

To a solution of (S)-tert-butyl 3-((R)-2-amino-1-hydroxyethyl)-3,4-dihydroisoquinoline-2(1H)-carboxylate I9 (200 mg, 0.68 mmol) in MeOH (2 mL) was added benzaldehyde (80 mg, 0.75 mmol). The mixture was stirred at room temperature for 2 hours then NaBH$_4$ (85 mg, 1.36 mmol) was added in portions. The mixture was stirred at room temperature for 2 hours then the solvent was removed and the residue dissolved in water (20 mL). The solution was adjusted to pH 10 by addition of 1.0 M aqueous NaOH solution and the aqueous layer extracted with DCM (3×20 mL). The combined organic extracts were washed with brine (30 mL), dried (Na$_2$SO$_4$), filtered and concentrated. The residue was purified by column chromatography (2% MeOH in DCM) to give the title compound as a yellow oil (120 mg, 46%). LCMS: RT 2.33 min; m/z 383.2 [M+H]⁺.

(b) (S)-tert-Butyl 3-((R)-2-(benzyl(methyl)amino)-1-hydroxyethyl)-3,4-dihydroisoquinoline-2(1H)-carboxylate (A10)

To a solution of (S)-tert-butyl 3-((R)-2-(benzylamino)-1-hydroxyethyl)-3,4-dihydroisoquinoline-2(1H)-carboxylate A9 (120 mg, 0.31 mmol) in CH$_3$OH (2 mL) was added 37% aqueous formaldehyde (150 µL, 1.55 mmol), NaBH$_3$CN (40 mg, 0.62 mmol) and AcOH (1 drop) and the reaction stirred at room temperature overnight. The solvent was removed and the residue dissolved in water (10 mL). The pH was adjusted to 10 by addition of 0.5 M aqueous NaOH and the aqueous extracted with EtOAc (3×20 mL). The combined organic fractions were dried (Na$_2$SO$_4$) and concentrated.

The residue was purified by preparative TLC (5% MeOH in DCM) to give the title compound as yellow oil (90 mg, 73%). LCMS: RT 2.23 min; m/z 397.2 [M+H]$^+$.

(c) (S)-tert-Butyl 3-((R)-1-hydroxy-2-(methylamino)ethyl)-3,4-dihydroisoquinoline-2(1H)-carboxylate (A11)

A mixture of (S)-tert-butyl 3-((R)-2-(benzyl(methyl)amino)-1-hydroxyethyl)-3,4-dihydroisoquinoline-2(1H)-carboxylate A10 (80 mg, 0.20 mmol) and Pd(OH)$_2$ (14 mg, 0.1 mmol) in EtOAc (2 mL) was stirred at 45° C. under a hydrogen atmosphere overnight. The catalyst was removed by filtration through Celite and the filtrate was concentrated. The residue obtained was purified by preparative TLC (7% MeOH/DCM) to give the title compound as a yellow oil (40 mg, 65%). LCMS: RT 2.19 min; m/z 307.2 [M+H]$^+$ (d) (3S)-tert-Butyl 3-((1R)-2-(4-(3-oxa-8-azabicyclo[3.2.1]octane-8-carbonyl)-2-ethoxy-N-methylbenzamido)-1-hydroxyethyl)-3,4-dihydroisoquinoline-2(1H)-carboxylate (A12)

To a solution of 4-(3-oxa-8-azabicyclo[3.2.1]octane-8-carbonyl)-2-ethoxybenzoic acid I20 (40 mg, 0.13 mmol) and (S)-tert-butyl3-((R)-1-hydroxy-2-(methylamino)ethyl)-3,4-dihydroisoquinoline-2(1H)-carboxylate A11 (40 mg, 0.13 mmol) in DCM was added DIPEA (75 mg, 0.59 mmol), HOBt (2 mg, 0.013 mmol), and EDCl.HCl (50 mg, 0.26 mmol). The resulting mixture was stirred at room temperature for two days. The mixture was diluted with DCM (20 mL) and the organic layer washed with saturated aqueous NaHCO$_3$ (20 mL), 0.5 M aqueous HCl (20 mL), water (20 mL) and brine (20 mL), dried (Na$_2$SO$_4$), filtered and concentrated. The residue obtained was purified by preparative TLC (5% MeOH in DCM) to give the title compound as a yellow solid (35 mg, 45%). LCMS: RT 2.80 min; m/z 594.3 [M+H]

(e) 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)-N-methylbenzamide hydrochloride (3)

To a solution of (3S)-tert-butyl 3-((1R)-2-(4-(3-oxa-8-azabicyclo[3.2.1]octane-8-carbonyl)-2-ethoxy-N-methylbenzamido)-1-hydroxyethyl)-3,4-dihydroisoquinoline-2(1H)-carboxylate A12 (30 mg, 0.05 mmol) in Et$_2$O (1 mL) was added HCl in Et$_2$O (1.8 M, 1 mL). The mixture was stirred at room temperature overnight. The solvent was removed and the solid washed with Et$_2$O (3×3 mL) to give the title compound as a yellow solid (23 mg, 85%). $^1$H NMR (400 MHz, MeOD) δ 7.34-7.32 (m, 5H), 7.14-7.06 (m, 2H), 4.62 (br s, 1H), 4.42-4.29 (m, 3H), 4.09-3.59 (m, 11H), 3.22-3.19 (m, 1H), 3.04 (br s, 3H), 1.99 (br s, 4H), 1.22 (br s, 3H), LCMS: RT 3.39 min; m/z 494.3 [M+H]$^+$.

Assays
PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-NH$_2$). Full-length PRMT5 enzyme (NCBI Reference sequence NP_006100.2) was co-expressed with His$_6$-MEP50 in insect cells and purified via Nickel immobilized metal affinity and gel filtration chromatography ("the enzyme").

The 6 μL reactions are run in Greiner brand black 384-well low volume assay plates. All reactions contained assay buffer (phosphate buffered saline, 0.01% (v/v) Tween-20, 0.01% (w/v) albumin from chicken egg white, 1 mM Dithiothreitol, 1 μM peptide substrate, 1 μM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37 degree Celsius. Reaction progress was measured using the Transcreener™ EPIGEN methyltransferase assay (Bell-Brook Labs, Madison, Wis.) as recommended by the manufacturer. To each reaction 2 μL detection mix were added, containing coupling enzymes, fluorescence polarisation tracer, and AMP antibody. Plates were incubated for 90 minutes before being read on a PerkinElmer EnVision™ plate reader in fluorescence polarisation mode. IC$_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I]$^D$)))) where A is the lower asymptote, B is the upper asymptote, C is the IC$_{50}$ value, and D is the slope.

| Compound Number | IC$_{50}$ (μM) |
|---|---|
| 1 | 0.019 |
| 2 | 0.019 |
| 3 | 0.036 |

PRMT5 Biomarker Assay

Compounds of the invention may be tested for potency to inhibit symmetrical dimethylation of arginine in the following assay:

The cell line TE11 was seeded at a density of 6,000 cells per well in 96 well optical quality tissue culture plates in DME medium and 10% foetal bovine serum, and allowed to adhere for 5 hours under standard culture conditions (37 degree Celsius, 5% CO$_2$). Compound dilutions prepared in DMSO were added to the medium, with negative control wells reserved for treatment with DMSO only and maximum inhibition controls receiving a potent PRMT5 inhibitor compound at 1 μM concentration. After incubation for 72 hours, the cells were fixed with 3.7% formaldehyde in PBS for 30 minutes at room temperature, washed with phosphate buffer saline and blocked with Odyssey blocking buffer (LI-COR, Lincoln, Nebr.). Rabbit anti-Di-Methyl Histone H4 Arginine 3 specific antibody (Epigentek) in Odyssey blocking buffer was added and incubated for 14 hours at 4 degree Celsius. After washing, anti-rabbit secondary antibody labelled with Alexa647 dye (LifeTechnologies) and Hoechst 33342 (1 μg/mL, SigmaAldrich) were added for 1 hour incubation. Plates were washed and read on a PerkinElmer Envision 2103 in fluorescence intensity scanning mode (24 scans across the well area). The plates were imaged on a PerkinElmer Phenix high content imaging platform. Using a Columbus image analysis pipeline, individual nuclei were located by Hoechst 33342 stain and the methylation level was calculated from the Alexa647-related intensity in the same area. IC$_{50}$ values were obtained from the mean Alexa647-related intensity per cell by calculating percent inhibition (% I) for each well relative to controls on the same plate (% I=(I−CN)/(CP−CN) where CN/CP are the averages of the negative/maximum inhibition controls, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope.

| Compound Number | IC$_{50}$ (μM) |
|---|---|
| 1 | 0.0039 |
| 2 | 0.0006 |
| 3 | 0.0117 |

The invention claimed is:

1. A compound of formula:

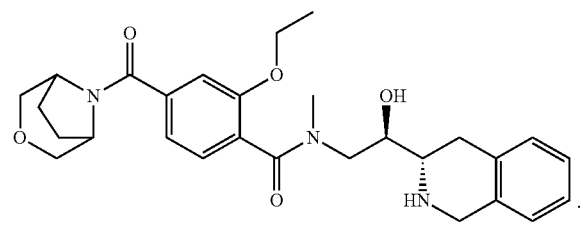 [SMILES: CCOc1cc(C(=O)N2C3CCC2COC3)ccc1C(=O)N(C)C[C@@H](O)[C@@H]1Cc2ccccc2CN1]

2. A method for the treatment of cancer, comprising administering to a patient in need of treatment, a therapeutically effective PRMT5 activity inhibiting amount of a composition comprising a compound of the following formula:

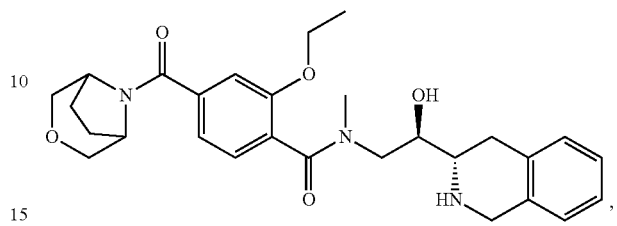

or pharmaceutically acceptable salts thereof; and a pharmaceutical carrier;

wherein the cancer is any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

* * * * *